(12) United States Patent
Melodia et al.

(10) Patent No.: US 10,271,728 B2
(45) Date of Patent: Apr. 30, 2019

(54) ULTRASONIC NETWORK FOR WEARABLE DEVICES

(71) Applicant: Northeastern University, Boston, MA (US)

(72) Inventors: Tommaso Melodia, Newton, MA (US); Giuseppe Enrico Santagati, Cambridge, MA (US)

(73) Assignee: Northeastern University, Boston, MA (US)

( * ) Notice: Subject to any disclaimer, the term of this patent is extended or adjusted under 35 U.S.C. 154(b) by 62 days.

(21) Appl. No.: 15/538,930

(22) PCT Filed: Jan. 26, 2016

(86) PCT No.: PCT/US2016/014814
§ 371 (c)(1),
(2) Date: Jun. 22, 2017

(87) PCT Pub. No.: WO2016/123047
PCT Pub. Date: Aug. 4, 2016

(65) Prior Publication Data
US 2017/0367578 A1 Dec. 28, 2017

Related U.S. Application Data

(60) Provisional application No. 62/107,737, filed on Jan. 26, 2015.

(51) Int. Cl.
*A61B 5/00* (2006.01)
*H04B 11/00* (2006.01)
(Continued)

(52) U.S. Cl.
CPC .......... *A61B 5/0015* (2013.01); *A61B 5/0024* (2013.01); *A61B 5/0026* (2013.01);
(Continued)

(58) Field of Classification Search
CPC .... H04B 11/00; G08B 21/0453; G16H 50/20; H04M 1/6066; H04W 4/08; H04W 52/0219; H04W 52/0251; H04W 8/22
See application file for complete search history.

(56) References Cited

U.S. PATENT DOCUMENTS 6,547,730 B1 4/2003 Lin et al.
7,733,224 B2 6/2010 Tran
(Continued)

FOREIGN PATENT DOCUMENTS

EP 0809366 B1 9/2007
WO 2013165474 A1 11/2013

OTHER PUBLICATIONS

Jain M et al. Practical, Real-time, Full Duplex Wireless. MobiCom'II, Sep. 19-23, 2011, Las Vegas, Nevada, USA.

*Primary Examiner* — Muhammad N Edun
*Assistant Examiner* — Jerold B Murphy

(57) ABSTRACT

An ultrasonic communication system and method provide a networking framework for wearable devices based on ultrasonic communications. The ultrasonic communication system and method incorporate a set of physical, data link, network and application layer functionalities that can flexibly adapt to application and system requirements to efficiently distribute information between ultrasonic wearable devices.

25 Claims, 14 Drawing Sheets

(51) Int. Cl.
*G16H 40/63* (2018.01)
*H04W 84/18* (2009.01)
*A61B 5/0205* (2006.01)
*A61B 5/024* (2006.01)

(52) U.S. Cl.
CPC .......... *A61B 5/0028* (2013.01); *G16H 40/63* (2018.01); *H04B 11/00* (2013.01); *H04W 84/18* (2013.01); *A61B 5/0205* (2013.01); *A61B 5/02438* (2013.01)

(56) References Cited

U.S. PATENT DOCUMENTS

| | | | |
|---|---|---|---|
| 8,301,232 B2 * | 10/2012 | Albert | A61B 5/0006 600/509 |
| 8,323,188 B2 | 12/2012 | Tran | |
| 8,323,189 B2 | 12/2012 | Tran | |
| 8,509,882 B2 * | 8/2013 | Albert | A61B 5/0404 600/509 |
| 8,747,336 B2 | 6/2014 | Tran | |
| 2003/0128746 A1 | 7/2003 | Lerner et al. | |
| 2004/0202339 A1 * | 10/2004 | O'Brien, Jr. | H04B 13/005 381/312 |
| 2006/0129375 A1 | 6/2006 | Lenz et al. | |
| 2006/0181421 A1 | 8/2006 | Forcier et al. | |
| 2007/0260709 A1 | 11/2007 | Dowling | |
| 2009/0041054 A1 | 2/2009 | Das et al. | |
| 2009/0180529 A1 | 7/2009 | Agazzi et al. | |
| 2010/0298669 A1 * | 11/2010 | Ida | A61B 5/0002 600/302 |
| 2012/0230326 A1 | 9/2012 | Ganeshalingam et al. | |
| 2013/0197320 A1 * | 8/2013 | Albert | A61B 5/02055 600/301 |
| 2013/0274563 A1 * | 10/2013 | Duesterhoft | A61B 5/4848 600/301 |
| 2014/0019830 A1 | 1/2014 | Chen et al. | |
| 2014/0128754 A1 * | 5/2014 | Luna | A61B 5/746 600/500 |
| 2014/0180111 A1 | 6/2014 | Gopinathan et al. | |
| 2014/0279528 A1 | 9/2014 | Slaby et al. | |
| 2015/0018660 A1 * | 1/2015 | Thomson | A61B 5/0404 600/393 |
| 2015/0261415 A1 * | 9/2015 | Lee | H04L 41/0803 715/716 |
| 2016/0174158 A1 * | 6/2016 | Vance | H04W 52/0251 455/418 |
| 2017/0284859 A1 * | 10/2017 | Bauer | G01N 29/024 |
| 2017/0284920 A1 * | 10/2017 | Bauer | G01N 29/024 |

* cited by examiner

ULTRASONIC NETWORK FOR WEARABLE DEVICES

CROSS REFERENCE TO RELATED APPLICATIONS

This application claims priority under 35 § 119(e) of U.S. Provisional Application No. 62/107,737 filed on Jan. 26, 2015, entitled "U-Wear: Software-Defined Ultrasonic Networking for Wearable Devices", the disclosure of which is hereby incorporated by reference.

STATEMENT REGARDING FEDERALLY SPONSORED RESEARCH OR DEVELOPMENT

The invention was developed with financial support from Grant No. CNS-1253309 from the National Science Foundation. The U.S. Government has certain rights in the invention.

BACKGROUND

Wearable medical sensing devices with wireless capabilities have become the cornerstone of many digital health applications that promise to predict and treat major diseases by acquiring and processing health information. Existing wireless wearable devices are connected through radio frequency processing (RF) electromagnetic wave carriers based on standards such as Bluetooth or Wi-Fi. However, these solutions tend to scale down traditional wireless technologies to the body environment, with little or no attention paid to the peculiar characteristics of the human body and the privacy and security requirements of patients.

SUMMARY OF THE INVENTION

A networking framework for wearable devices is provided based on ultrasonic communications. More particularly, an ultrasonic communication system and method incorporate a set of physical, data link and network layer functionalities that can flexibly adapt to application and system requirements to efficiently distribute information between ultrasonic wearable devices. The communication system and method offer real-time reconfiguration functionalities at the application layer to add flexibility to the medical monitoring experience.

The system relates to a communication framework for communicatively connecting wearable body sensors, medical devices, and external computing devices using ultrasonic frequencies. The system is based on a software platform that can arrange the various sensors and devices in a node configuration, including peer to peer or master/slave configurations. Each node in the system can access the software platform to exchange and collect information/data with other nodes in the system or from a central database. The exchange of information between the various nodes can enhance the monitoring and sensing capabilities, for example, to allow one node to request measurements from a specific sensor or device in the system. The system allows for real-time reconfiguration to modify an existing application or install a new application on each of the nodes in the system to measure or monitor various characteristics of a user or perform various actions.

Other aspects of the method and system include the following:
1. A system for transmitting data ultrasonically among wearable devices comprising:
   a network comprising a plurality of nodes, at least a portion of the nodes wearable by a user, each of the wearable nodes including a wearable sensor or a wearable actuator; and
   a first node of the plurality of nodes comprising:
      a communication unit comprising an ultrasonic transceiver to transmit and receive in-air ultrasonic signals;
      a processing unit in communication with the communication unit to receive signals from and transmit signals to the communication unit, the processing unit including one or more processors and memory; and
      a protocol stack disposed within the processing unit, the protocol stack comprising a plurality of layers through which a data packet is transmitted to enable ultrasonic communication among the plurality of nodes.
2. The system of item 1, wherein the protocol stack includes a physical layer, a data link layer, and a network layer.
3. The system of any of items 1-2, wherein the protocol stack further includes an application layer.
4. The system of item 3, wherein the processing unit is operative at the application layer of the protocol stack to reconfigure parameters at a physical layer of the protocol stack.
5. The system of any of items 3-4, wherein the processing unit is operative at the application layer of the protocol stack to execute an application.
6. The system of any of items 3-5, wherein the processing unit is operative at the application layer to specify an input comprising data generated at a sensor associated with a wearable node.
7. The system of any of items 3-6, wherein the processing unit is operative at the application layer to specify an output comprising a measured parameter for storage in the memory or transmission to another node.
8. The system of any of items 3-7, wherein the processing unit is operative at the application layer to carry out one or more data processing operations.
9. The system of item 8, wherein each data processing operation is identified with a key, and a concatenation of keys forms an application.
10. The system of any of items 8-9, wherein the data processing operations are defined by one or more primitive blocks at a physical layer of the protocol stack, the primitive blocks comprising one or more of a filter, a data operation block, and a detector.
11. The system of item 10, wherein the processing unit is operative at the application layer to arrange a plurality of the primitive blocks in a user-selected order.
12. The system of any of items 10-11, wherein the filter is operative to filter raw data to remove one or more of offset, drift of a sensor, or a noise component from an external source.
13. The system of any of items 10-12, wherein the data operation block is operative to perform one or more signal processing operations on data received from a sensor.
14. The system of item 13, wherein the signal processing operations include an arithmetic operation, a correlation operation, a convolution operation, a counting operation, or a Fourier transform operation.
15. The system of any of items 10-14, wherein the detector is operative to measure a desired parameter in a processed signal.
16. The system of item 15, wherein the desired parameter includes one or more of a peak, a pattern, or a time interval.
17. The system of any of items 3-16, wherein the processing unit is operative at the application layer to fetch data from an external source or from another node in the network.

18. The system of any of items 3-17, wherein the processing unit is operative at the application layer to push data or an actuating command to another node in the network.

19. The system of any of items 3-18, wherein the processing unit is operative at the application layer to provide a graphical user interface to display a selection of applications or functionalities within the protocol stack.

20. The system of any of items 3-19, wherein the processing unit is operative at the application layer to provide speech recognition.

21. The system of any of items 1-20, wherein the processing unit is operative at a physical layer of the protocol stack to provide forward error correction.

22. The system of item 21, wherein the forward error correction comprises addition of parity symbols using a block code or a convolution code.

23. The system of any of items 21-22, wherein the forward error correction comprises a Reed-Solomon encoder operative to add t parity symbols to k information symbols to make an n symbol block, and a Reed Solomon decoder to decode a received n-symbol block and correct up to t/2 data symbols.

24. The system of any of items 21-23, wherein the processing unit is operative at a data link layer of the protocol stack to adapt the physical layer to select a forward error correction coding rate to minimize a number of retransmissions.

25. The system of any of items 1-24, wherein the processing unit is operative at a physical layer of the protocol stack to provide a zero-forcing equalizer comprising a finite-impulse-response filter that for each input symbol, forces to zero any intersymbol interference components introduced by adjacent symbols.

26. The system of any of items 1-25, wherein the processing unit is operative at a physical layer of the protocol stack to calculate filter taps numerically beginning from an estimate of a channel impulse response.

27. The system of any of items 1-26, wherein the processing unit is operative at a physical layer of the protocol stack to provide a pseudo noise sequence or a chirp signal as a preamble of the data packet.

28. The system of any of items 1-27, wherein the processing unit is operative at a physical layer of the protocol stack to correlate a received signal with a known preamble sequence to obtain an estimate of a time-domain channel impulse response.

29. The system of any of items 1-28, wherein the processing unit is operative at a physical layer of the protocol stack to provide narrow band Gaussian minimum shift keying (GMSK) modulation or demodulation.

30. The system of any of items 1-29, wherein the processing unit is operative at a physical layer of the protocol stack to provide wideband orthogonal frequency division multiplexing for modulation or demodulation.

31. The system of any of items 1-30, wherein the processing unit is operative at a physical layer of the protocol stack to provide narrow band Gaussian minimum shift keying (GMSK) modulation or demodulation or to provide wideband orthogonal frequency division multiplexing for modulation or demodulation.

32. The system of any of items 1-31, wherein the processing unit is operative at upper layers of the protocol stack to modify one or more parameters at a physical layer of the protocol stack, the parameters comprising a modulation rate, a signal bandwidth, and forward error correction coding rate.

33. The system of any of items 1-32, wherein the processing unit is operative at a data link layer of the protocol stack to provide polling to coordinate access to communication links among the nodes.

34. The system of any of items 1-33, wherein the processing unit is operative at a data link layer of the protocol stack to provide an ALOHA access protocol to coordinate access to communication links among the nodes.

35. The system of any of items 1-34, wherein the processing unit is operative at a data link layer of the protocol stack to provide carrier sense multiple access with collision avoidance to coordinate access to communication links among the nodes.

36. The system of any of items 1-35, wherein the processing unit is operative at a data link layer of the protocol stack to provide forward error correction coding rate reactive adaptation.

37. The system of any of items 1-36, wherein the processing unit is operative at a network layer of the protocol stack to provide content centric addressing, comprising providing a content object at one of the nodes with an identification by which the content object can be accessed by others of the nodes.

38. The system of item 37, wherein the content object comprises sensor data or an actuation command.

39. The system of any of items 1-38, wherein the processing unit is operative at a network layer of the protocol stack to provide header information for transmission to a device on another network.

40. The system of item 39, wherein the processing unit is operative at the network layer to provide IP header compression and IP packet fragmentation.

41. The system of any of items 39-40, wherein the header information includes an Internet Protocol address for identification and location of the device on the other network.

42. The system of any of items 39-41, wherein the other network comprises the Internet.

43. The system of any of items 39-42, wherein the header information is compatible with Internet Protocol version 4 or Internet Protocol version 6.

44. The system of any of items 1-43, wherein the plurality of nodes are connected in a peer-to-peer configuration.

45. The system of any of items 1-44, wherein the plurality of nodes are connected in a master-slave configuration, and the first node comprises a master node.

46. The system of item 45, wherein the master node is operative to transmit an application to a further node in the network.

47. The system of any of items 45-46, wherein the master node is disposed on an external computing device.

48. The system of item 47, wherein the external computing device comprises a smart phone, a tablet, a laptop, a desktop computer, a personal computer, a smart watch, smart glasses, or smart clothing.

49. The system of any of items 1-48, wherein the plurality of nodes includes a node implantable within biological tissue.

50. The system of any of items 1-49, wherein the biological tissue is human tissue or animal tissue.

51. The system of any of items 1-50, wherein the wearable sensor comprises a sensor operative to sense a biological parameter.

52. The system of any of items 1-51, wherein the wearable sensor is selected from the group consisting of a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality.

53. The system of item 52, wherein the sensor for one or more biomolecules comprises a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

54. The system of any of items 1-53, wherein the wearable actuator is selected from the group consisting of a drug pump, a heart stimulator, a heart pacemaker, a bone growth stimulator, a deep brain stimulator, a neurostimulator, and a neuromuscular electrical stimulator.

55. The system of any of items 1-54, wherein the first node comprises a wearable node.

56. The system of any of items 1-55, wherein the ultrasonic transceiver comprises a piezoelectric transducer or an electrostatic transducer.

57. The system of any of items 1-56, wherein the ultrasonic transceiver comprises a micromachined ultrasonic transducer.

58. The system of any of items 1-57, wherein the ultrasonic transceiver comprises an air-coupled ultrasonic transducer.

59. The system of any of items 1-58, wherein the ultrasonic transceiver comprises a microphone and a speaker.

60. The system of any of items 1-59, wherein the ultrasonic transceiver is operable to transmit and receive ultrasonic or near-ultrasonic signals at frequencies above at least about 15 kHz.

61. The system of any of items 1-60, wherein the ultrasonic transceiver is operable to transmit and receive ultrasonic or near-ultrasonic signals at frequencies above at least about 17 kHz.

62. The system of any of items 1-61, wherein the ultrasonic transducer is operable to transmit and receive ultrasonic signals at frequencies above at least about 20 kHz.

63. The system of any of items 1-62, wherein the first node further comprises:
an analog-to-digital converter disposed to convert analog signals from the communication unit to digital signals for transmission to the processing unit, and
a digital-to-analog converter disposed to convert digital signals from the processing unit to analog signals for transmission to the communication unit.

64. The system of any of items 1-63, wherein the processing unit comprises a microprocessor or microcontroller.

65. The system of any of items 1-64, wherein the communication unit further comprises a power amplifier in a transmit chain and a low noise amplifier in a receive chain.

66. The system of any of items 1-65, further comprising a power unit operative to provide power to the first node.

67. The system of item 66, wherein the power unit comprises a battery.

68. The system of item 67, further comprising a wireless energy transfer unit operative to utilize ultrasonic power transmission to charge the battery.

69. The system of any of items 1-68, wherein at least two of the plurality of nodes are wearable by the user.

70. The system of any of items 1-69, wherein at least three of the plurality of nodes are wearable by the user.

71. The system of any of items 1-70, wherein at least one of the nodes of the plurality of nodes is implantable within a body.

72. A method for transmitting data ultrasonically among wearable devices comprising:
providing a node comprising:
a communication unit comprising an ultrasonic transceiver to transmit and receive in-air ultrasonic signals, and
a processing unit in communication with the communication unit, comprising one or more processors and memory, and a protocol stack comprising a plurality of layers through which a data packet is transmitted;
coding or decoding a data packet by transmission through the layers of the protocol stack within the processing unit; and
transmitting an ultrasonic signal to or receiving an ultrasonic signal from another node.

73. The method of item 72, further comprising directing an application layer of the protocol stack to reconfigure parameters at a physical layer of the protocol stack.

74. The method of any of items 72-73, further comprising executing an application at an application layer of the protocol stack.

75. The method of item 74, further comprising specifying at the application layer an input comprising data generated at a sensor associated with a wearable node or an output comprising a measured parameter for storage in the memory or transmission to another node.

76. The method of any of items 74-75, further comprising performing one or more data processing operations at the application layer.

77. The method of any of items 76, further comprising identifying each of a plurality of data processing operations with a key, and concatenating a number of keys to form an application.

78. The method of any of items 76-77, wherein the data processing operations are defined by one or more primitive blocks at a physical layer of the protocol stack, the primitive blocks comprising one or more of a filter, a data operation block, and a detector.

79. The method of item 78, further comprising arranging a plurality of the primitive blocks in a user-selected order at the application layer.

80. The method of any of items 72-79, further comprising filtering raw data to remove one or more of offset, drift of a sensor, or a noise component from an external source.

81. The method of any of items 72-80, further comprising performing one or more signal processing operations on data received from a sensor.

82. The method of item 81, wherein the signal processing operations include an arithmetic operation, a correlation operation, a convolution operation, a counting operation, or a Fourier transform operation.

83. The method of any of items 81-82, further comprising measuring a desired parameter in a processed signal.

84. The method of item 83, wherein the desired parameter includes one or more of a peak, a pattern, or a time interval 85. The method of any of items 72-84, further comprising, at the application layer, fetching data from an external source or from another node in the network or pushing data or an actuating command to another node in the network.

86. The method of any of items 72-85, further comprising providing a graphical user interface to display a selection of applications or functionalities within the protocol stack.

87. The method of any of items 72-86, further comprising providing speech recognition at an application layer of the protocol stack.
88. The method of any of items 72-87, further comprising coding the data packet with a forward error correction code at a physical layer of the protocol stack.
89. The method of item 88, further comprising adding parity symbols using a block code or a convolution code.
90. The method of any of items 88-89, further comprising selecting a coding rate to minimize a number of retransmissions of the data packet.
91. The method of any of items 72-90, further comprising forcing to zero any intersymbol interference components introduced by adjacent symbols.
92. The method of any of items 72-91, further comprising calculating filter taps numerically beginning from an estimate of a channel impulse response.
93. The method of any of items 72-92, further comprising providing a pseudo noise sequence or a chirp signal as a preamble of the data packet.
94. The method of any of items 72-93, further comprising correlating a received signal with a known preamble sequence to obtain an estimate of a time-domain channel impulse response.
95. The method of any of items 72-94, further comprising modulating or demodulating the signal with narrow band Gaussian minimum shift keying.
96. The method of any of items 72-95, further comprising modulating or demodulating the signal with orthogonal frequency division multiplexing.
97. The method of any of items 72-96, further comprising modifying at an upper layer of the protocol stack one or more parameters at a physical layer of the protocol stack, the parameters comprising a modulation rate, a signal bandwidth, and a forward error correction coding rate.
98. The method of any of items 72-97, further comprising polling a plurality of neighboring nodes to coordinate access to communication links among the neighboring nodes.
99. The method of any of items 72-98, further comprising providing an ALOHA access protocol or carrier sense multiple access with collision avoidance to coordinate access to communication links among the nodes.
100. The method of any of items 72-99, further comprising providing forward error correction coding rate reactive adaptation.
101. The method of any of items 72-100, further comprising providing a content object at one of the nodes with an identification by which the content object can be accessed by others of the nodes.
102. The method of item 101, wherein the content object comprises sensor data or an actuation command.
103. The method of any of items 72-102, further comprising providing header information for transmission to a device on another network.
104. The method of item 103, further comprising providing IP header compression and IP packet fragmentation.
105. The method of any of items 103-104, wherein the header information includes an Internet Protocol address for identification and location of the device on the other network.
106. The method of any of items 103-105, wherein the other network comprises the Internet.
107. The method of any of items 103-106, wherein the header information is compatible with Internet Protocol version 4 or Internet Protocol version 6.
108. The method of any of items 72-107, further comprising transmitting or receiving an ultrasonic signal representative of sensor data received from a wearable sensor.
109. The method of any of items 72-108, further comprising transmitting an ultrasonic signal representative of an actuating command to a node that comprises a wearable actuator.
110. The method of any of items 72-109, further comprising transmitting an ultrasonic signal through air, or receiving an ultrasonic signal that has passed through air.
111. The method of any of items 72-110, further comprising transmitting an ultrasonic signal through biological tissue, or receiving an ultrasonic signal that has passed through biological tissue.

DESCRIPTION OF THE DRAWINGS

The invention will be more fully understood from the following detailed description taken in conjunction with the accompanying drawings in which.

DETAILED DESCRIPTION OF THE INVENTION

Radio frequency technology presents a number of limitations when adapted to wearable devices. First, the RF frequency spectrum is scarce, strictly regulated, and already crowded with many devices interfering with one another.

Therefore, RF-based technologies raise serious concerns about potential interference from existing RF communication systems that can unintentionally undermine the reliability and security of a wearable network, and ultimately the safety of the patient. Also, RF communications can be easily jammed, i.e., intentionally disrupted by artificially generated interference, or eavesdropped by malicious agents. This raises major privacy and security concerns for wearable networks, and a risk for the patient. Additionally, the medical community is still divided on the risks caused by continuous exposure of human tissues to RF radiation. Therefore, a massive deployment of RF wearable devices on the body may represent a potential risk for the patient. Further, the dielectric nature of the human body also affects the coupling between on-body RF antennas and the body itself. In particular, the gain and the radiation pattern of the antenna deteriorate because of the contact or proximity with the human body while the resonant frequency and the input impedance of the antenna may shift from their nominal values.

Figure 1:
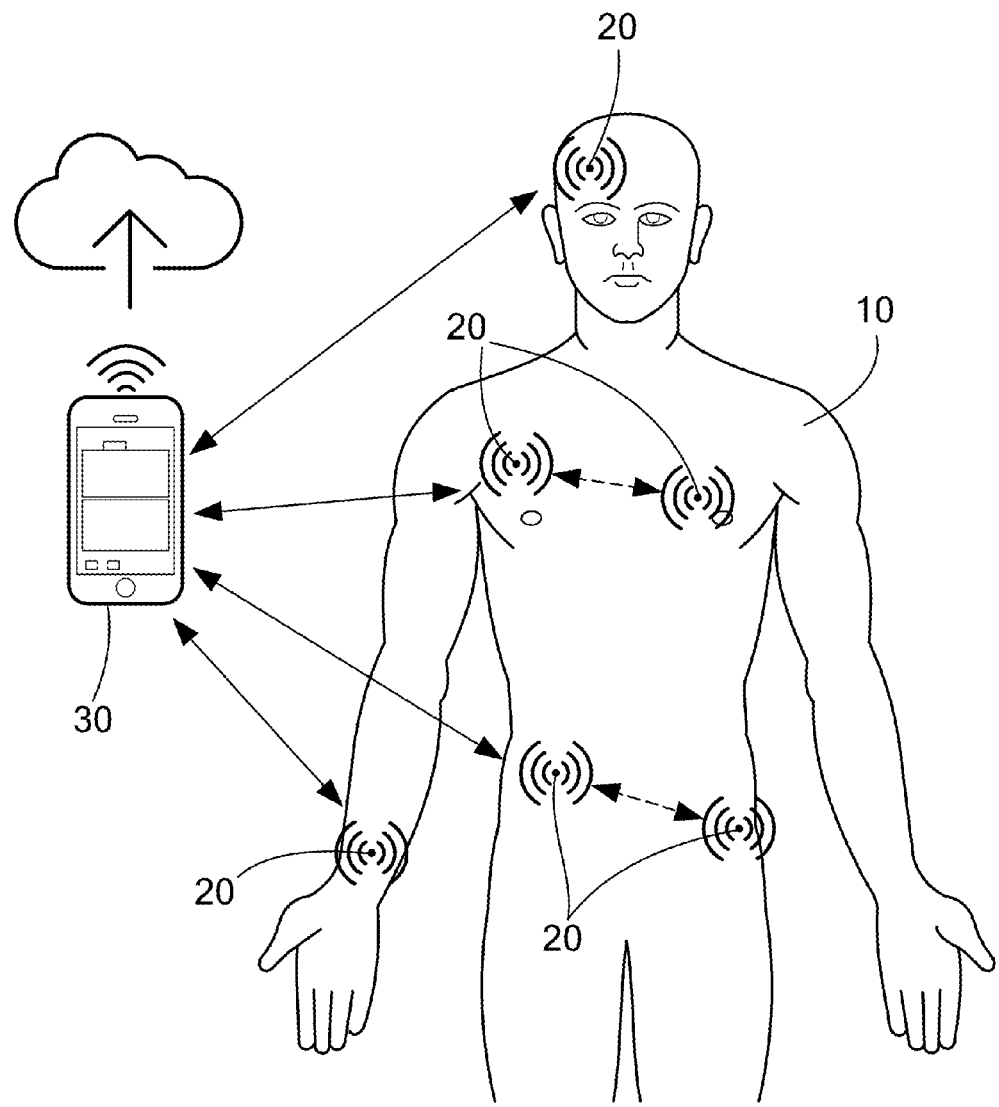
FIG. 1 is a schematic illustration of an ultrasonic communication system for transmitting data ultrasonically among wearable devices.

Accordingly, a communication system and method are described herein that use ultrasonic waves to interconnect wearable devices and that employ a software-defined networking framework. Ultrasonic waves are acoustic waves with frequency higher than the upper threshold for human hearing (nominally 20 kHz). Referring to FIG. 1, a human body 10 is illustrated with a network of wearable nodes 20 that can communicate ultrasonically with each other and with a node 30 that is located off the body, such as in a smart phone or other device.

The present ultrasonic communication system has several advantages over traditional networking frameworks based on RF communications. The system eliminates any potential conflict with existing RF communication systems and overcrowded RF environments. The ultrasonic frequency spectrum is currently unregulated, giving high flexibility to the system in terms of ultrasonic spectrum allocation. The system enables nodes to flexibly adapt the occupied frequency to specific requirements, such a maximum level of tolerable co-channel interference, maximum tolerable channel multipath and Doppler spreading in the channel and minimum data rate needed at the application layer. As compared to RF waves, ultrasonic waves do not easily penetrate in solid materials and do not propagate far in air; therefore, the ultrasonic communication system is inherently more secure with respect to eavesdropping and jamming attacks, which require close proximity. The medical experience of the last decades has demonstrated that ultrasounds are fundamentally safe, as long as acoustic power dissipation in tissues is limited to predefined safety levels. By equipping wearable devices with ultrasonic transducers, the present system can also implement ultrasonic power transmission schemes that enable wireless battery charging functionalities. On-board ultrasonic transducers can also be used to enable acoustic localization and tracking functionalities, which have better accuracy than RF-based systems because of the low propagation speed of sound in air. The low-propagation speed of sound also eases detection in the presence of strong multipath with respect to RF waves, because of the higher difference in propagation time between multiple paths. The system can be interfaced with ultrasonic intra-body networks, and can work as a bridge between intra-body sensors and the external world. The software-defined framework can run on general-purpose hardware; thus, it can enable commercial devices, such as smartphones, laptops and smart-TVs, to communicate with ultrasonic wearable devices in the near-ultrasonic frequency range, i.e., from 15 or 17 kHz to 20 or 22 kHz, using commercial-off-the-shelf (COTS) speakers and microphones. The software-defined ultrasonic networking functionalities can be reconfigured to adapt to application requirements, offering more flexibility with respect to traditional RF-based networking systems entirely implemented in hardware, e.g., Bluetooth or Wi-Fi.

The system includes a set of software-defined cross-layer functionalities tailored for networking ultrasonic wearable devices that offer real-time reconfigurability at different layers of the protocol stack, i.e., the physical (PHY), data link, network and application layer. More specifically, the system encloses a set of PHY, data link and network functionalities that can flexibly adapt to the application and system requirements, to optimally network information between ultrasonic wearable devices. The system also offers real-time reconfiguration at the application layer to provide a flexible platform to develop medical applications. In particular, the system includes sensor data processing applications running in nodes of a network that can be decomposed into primitive building blocks that can be arbitrarily arranged to create new sensing applications to fit the user requirements.

Embodiments of the system and method employ aspects at different layers of the protocol stack to overcome limitations posed by the propagation characteristics of ultrasonic waves in air. For example, two signaling schemes (GMSK and orthogonal frequency-division multiplexing (OFDM), discussed further below) can be suitably used because of their high spectral efficiency and resilience to multipath. Two different synchronization modes can be alternatively and suitably used for channels strongly affected by multipath or by Doppler effect. Upper layer protocols and functionalities can be selected to address challenges posed by the long propagation delays of ultrasounds in air that might prevent accurate timing.

1. Ultrasonic Airborne Communications

Ultrasounds are mechanical pressure waves that propagate through elastic media at frequencies above the upper limit for human hearing, i.e., 20 kHz.

Attenuation.

Two mechanisms mainly contribute to acoustic attenuation in air, i.e., spreading loss and absorption loss. The former includes spherical spreading, i.e., the acoustic pressure falls off proportionally to the surface area of a sphere. The latter is mainly related to atmospheric absorption caused by the interaction of the acoustic wave with the gas molecules of the atmosphere and is frequency, temperature, and humidity dependent.

For a signal at frequency f [Hz] over a transmission distance d [m], the attenuation can be expressed in [dB] as $$A_{dB} = 20 \log_{10}(d) + d\alpha(f), \quad (1)$$

where $\alpha(f)$ [dB/m] is the absorption coefficient, which increases quadratically with the frequency, but also depends on the ambient atmospheric pressure, temperature, and the molar concentration or water vapor, i.e., humidity.

Propagation Speed.

The propagation speed of acoustic waves in air is approximately 343 m/s at a temperature of 20° C. and at atmospheric pressure of 101.325 kPa, as compared to $3 \times 10^8$ m/s for RF electromagnetic waves. The speed of sound in air increases with temperature and humidity, going from 331 m/s at a temperature of 0° C. and 10% relative humidity to 351 m/s at a temperature of 30° C. and 90% relative humidity.

Doppler Spreading.

Doppler spreading occurs as a result of Doppler shifts caused by relative motion between source and receiver, and is proportional to their relative velocity. Doppler spreading generates two different effects on signals: a simple frequency translation, and a continuous spreading of frequencies that generates intersymbol interference (ISI), thus causing degradation in the communication performance. Since the speed of sound is several orders of magnitude lower than the speed of electromagnetic waves, the resulting Doppler effect is severe, even at relatively low speeds.

Reflections and Scattering.

The on-body ultrasonic channel is composed of several interfaces between air and human body, and between air and on-body and near-body objects. Because of this inhomogeneous pattern, the on-body channel can be modeled as an environment with pervasive presence of reflectors and scatterers. The direction and magnitude of the reflected wave depend on the orientation of the boundary surface and on the acoustic impedance of the different media involved. Scattered reflections occur when an acoustic wave encounters an object that is relatively small with respect to its wavelength. (The acoustic impedance is defined as the product between the density of a medium p and the speed of sound in the medium c.) Consequently, the received signal is obtained as the sum of numerous attenuated, possibly distorted, and delayed versions of the transmitted signal.

Ultrasonic Transducers.

An ultrasonic transducer is a device that converts electrical signals into ultrasonic signals and vice versa. Ultrasonic transducers can be categorized into two main classes based on the physical mechanism that enables the conversion, i.e., piezoelectric and electrostatic transducers. A piezoelectric transducer produces a mechanical vibration through a thin piezoelectric element under an external voltage variation, and produces a voltage variation under an external mechanical vibration. In electrostatic transducers the fundamental mechanism is the vibration of a thin plate under electrostatic forces.

When sound passes across an interface between two materials, it is in part transmitted and in part reflected. To maximize the acoustic energy radiated by the transducer, the acoustic impedance of the radiating surface should match the acoustic impedance of the propagation medium. Today, microelectro-mechanical (MEMS) technology has enabled the fabrication of microscopic piezoelectric and electrostatic transducers, i.e., so-called Micromachined Ultrasonic Transducers (MUTs). With MUTs, the acoustic impedance can be controlled to match the external medium by manipulating the device geometry. This characteristic makes MUTs suitable for air-coupled applications.

In some embodiments, the system can also include an array of transducers to enable directional communications with spatial filtering capabilities, i.e., beamforming. Ultrasonic arrays are transducers with multiple and independent active elements. By delaying in time the signal transmitted by each array element, an ultrasonic beam can be steered towards a specific direction, while at the receiver, spatial filtering can be used to receive the signal coming from a preferred direction while suppressing other directions. This process, known as beamforming, can be leveraged to dynamically adapt the transducer radiation pattern.

When the operating frequency of the ultrasonic communications falls in the near-ultrasonic frequency range, i.e., 15 to 17 kHz to 20 to 22 kHz, acoustic waves can be recorded and generated using components, such as microphones and speakers, which can be commercial off the shelf (COTS) components. Even though COTS components are often designed to operate a lower frequencies, i.e., at 0-17 kHz, they can still sense and generate, albeit less efficiently, near-ultrasonic frequency waves. Since many commercial devices such as smartphones, tablets and laptops among others, are equipped with audio interfaces, they can in some embodiments, support near-ultrasonic communications with no additional hardware.

2. System Architecture

The system comprises a set of software-defined multi-layer functionalities that can be implemented on general-purpose processing units, e.g., microprocessors, microcontrollers or FPGAs, among others, to enable networking operations between wearable devices equipped with airborne ultrasonic connectivity, i.e., air-coupled ultrasonic transducers, and sensing capabilities, i.e., sensors.

Figure 2:
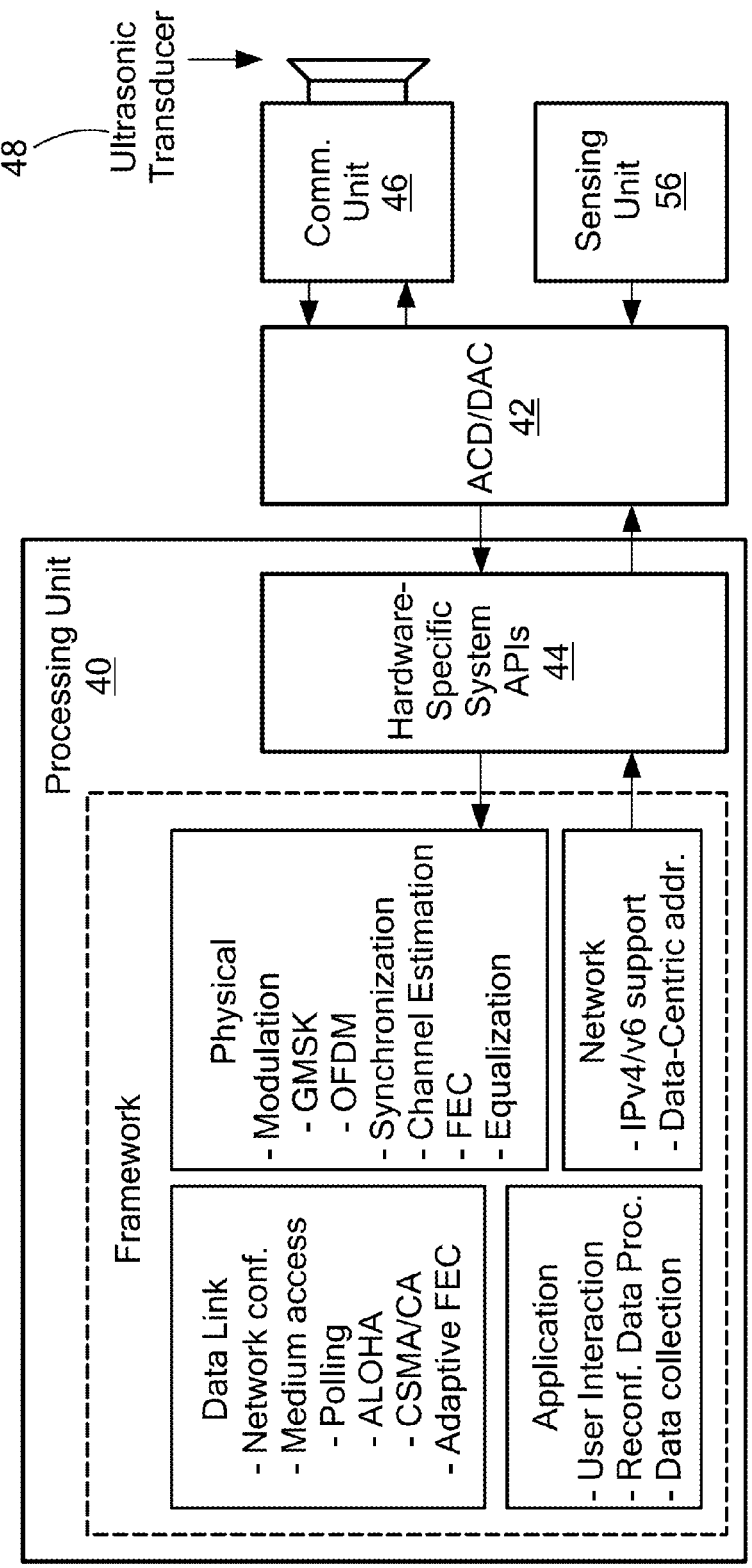
FIG. 2 is a schematic block diagram of a networking framework of the ultrasonic communication system.
Figure 3:
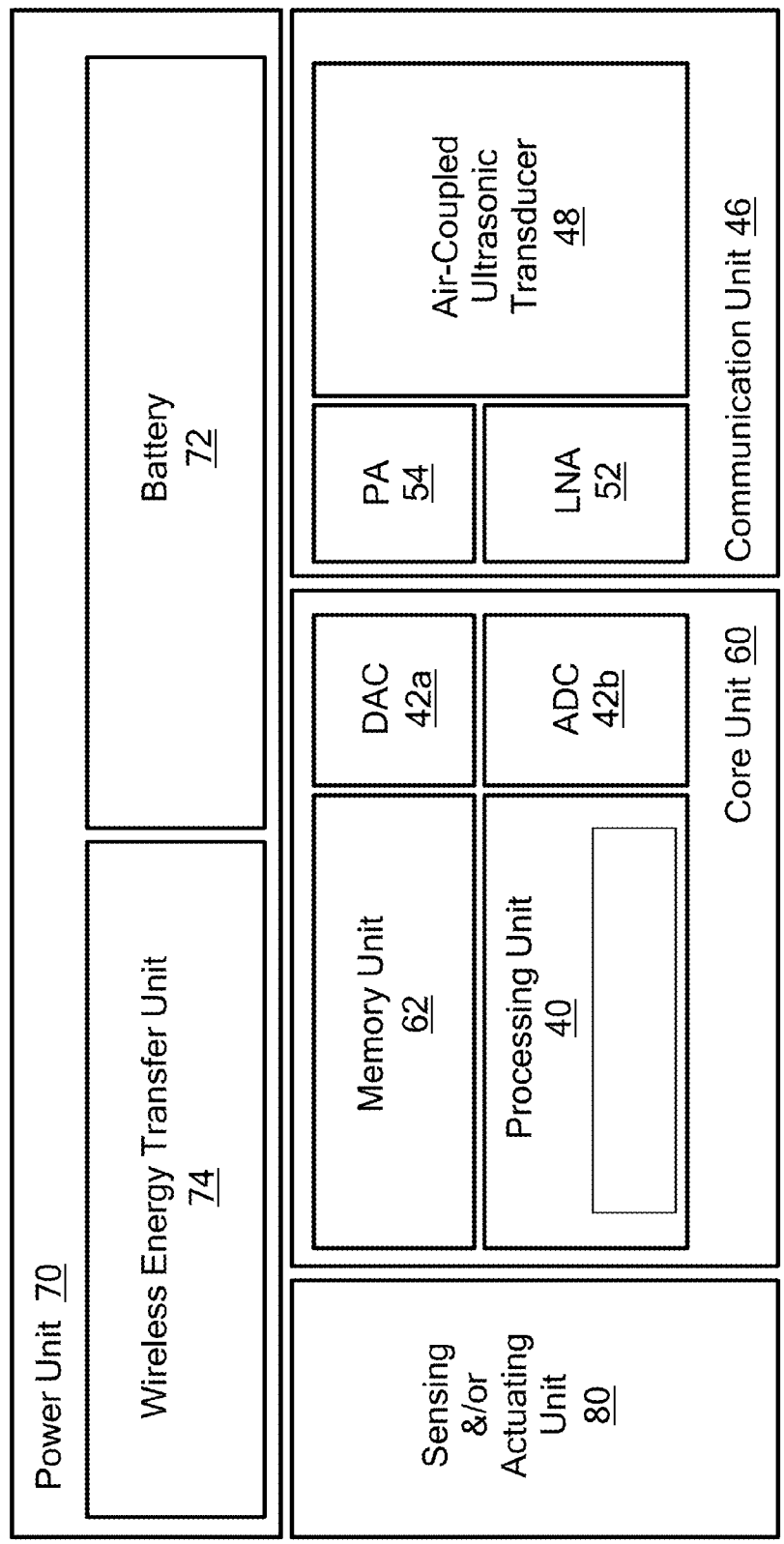
FIG. 3 is a schematic block diagram of a hardware embodiment of the ultrasonic communication system.

FIG. 2 shows an embodiment of an overview of the framework architecture, and FIG. 3 shows an embodiment of the hardware architecture. The system runs on a processing unit 40, which can access a hardware analog-to-digital converter (ADC) and digital-to-analog converter (DAC) 42 through hardware-specific system application programming interfaces (APIs) 44. In the transmission (Tx) chain, the DAC 42a collects and digital-to-analog converts the digital outputs, i.e., the waveforms to be transmitted generated by the processing unit, before passing these to a communication unit 46. In the receiving (Rx) chain, the ADC 42b analog-to-digital converts and passes to the processing unit the received waveforms coming from the communication unit 46. The communication unit includes an ultrasonic transceiver, for example, an ultrasonic transducer 48 and an amplification stage, i.e., a preamplifier 52 in the Rx chain and a power amplifier 54 in the Tx chain. The processing unit also collects the analog-to-digital converted data coming from a sensing unit 56. The communication framework at the processing unit comprises (i) physical (PHY) layer functionalities, e.g., modulation and synchronization, (ii) data link layer functionalities including forward error control or medium access control (MAC) protocols, (iii) network layer functionalities, e.g., IPv4 and IPv6 support and content-centric networking, and (iv) application layer functionalities, i.e., reconfigurable sensing data processing and user interface.

2.1 Physical Layer

The communication framework PHY layer defines the signaling scheme, channel estimation, equalization, synchronization and forward error correction (FEC) functionalities.

2.1.1 Signaling Schemes

In some embodiments, the framework can employ two fully-functional signaling schemes, a narrowband scheme based on Gaussian minimum-shift keying (GMSK) modulation, and a wideband scheme based on orthogonal frequency-division multiplexing (OFDM). Moreover, the framework includes a set of software-defined primitive blocks, e.g., programmable filters, and Fast Fourier Transform (FFT) modules, among others, that can be used to implement additional signaling schemes.

Narrowband GMSK.

GMSK is a continuous-phase modulation (CPM) used in GSM cellular systems. In frequency-shift keying (FSK) and phase-shift keying (PSK) the information is encoded in the variations of the carrier frequency or carrier phase, respectively. Since frequency and phase switches occur instantaneously, FSK and PSK signals do not have continuous phase. Phase discontinuity generates out-of-band power, leading to poor spectral efficiency. Moreover, in near-ultrasonic transmissions based on COTS speakers and microphones, the out-of-band power introduces audible noise (clicks), which make the communication perceptible to humans.

GMSK signals have instead phase continuity, and each symbol is represented by a phase variation, from the starting value to a final value, over the symbol duration, i.e., phase trajectory. Thus, the initial phase of each symbol is determined by the cumulative total phase variation of all previous symbols, i.e., there is phase memory. A Gaussian filter is used to smooth the phase trajectory and improve the spectral efficiency. The product between the signal bandwidth B and the symbol time T is a measure of the scheme spectral efficiency. A lower BT product leads to higher spectral efficiency, but increases the intersymbol interference (ISI). Based on these characteristics, GMSK is a suitable signaling scheme for the narrowband communications in the near-ultrasonic frequency range, which may use, for example, COTS speakers and microphones. Due to its phase-continuity, GMSK enables click-free transmissions, which can be advantageous over non-continuous-phase modulations such as frequency shift keying (FSK) and phase shift keying (PSK).

Wideband OFDM.

OFDM provides robustness against frequency selective channels with long delay spreads. The principle of OFDM is to use a large number of closely spaced orthogonal sub-carriers, such that for each sub-carrier the channel is subject to flat fading. In each sub-carrier a conventional modulation scheme can be used, such as M-PSK and M-Quadrature-Amplitude-Modulation (QAM). OFDM offers high spectral efficiency and robustness against narrowband co-channel interference, intersymbol interference (ISI) and multipath fading effect. OFDM can be efficiently implemented using FFT and inverse FFT (IFFT) algorithms. These characteristics make OFDM suitable for ultrasonic communications based on wideband transducers.

2.1.2 Synchronization

Synchronization in the communications framework can be achieved in two steps. First, an energy collection approach identifies any incoming packet, i.e., coarse synchronization. Once a packet is detected, the receiver performs a fine synchronization operation that identifies the exact starting point of the packet. Fine synchronization is achieved by correlating the received signal with a local copy of the preamble, i.e., a sequence that precedes each packet, which outputs a peak corresponding to the first sample of the packet.

Two synchronization modes can suitably be used in the present communications framework:

PN-Sequence Mode.

The pseudo noise (PN)-sequence mode uses PN-sequences as a preamble, i.e., binary sequences with sharp autocorrelation peak and low cross-correlation peaks, that can be deterministically generated. In one embodiment, maximum length sequences (MLSs), a particular family of PN-sequences are used. MLSs can be generated in software and hardware through linear feedback shift registers (LFSRs). Because of the desirable correlation characteristics, PN-sequences are suitable for enabling strong resilience to multipath, as in ultrasonic in-air communications.

Chirp-Based Mode.

The chirp-based mode uses a chirp signal as preamble, i.e., a sinusoidal waveform whose frequency varies from an initial frequency $f_0$ to a final frequency $f_1$ within a certain time T. Chirp signals provide good auto-correlation and robustness against Doppler effect. A frequency-shifted chirp can correlate well with the original chirp, although with lower amplitude and time-shifted peak. This characteristic makes chirp synchronization desirable for ultrasonic in-air communications under severe Doppler effect conditions, for example, fast moving sensor nodes worn by athletes for performance monitoring. The price for the Doppler robustness is higher cross-correlation peaks compared to PN-sequences that result in lower resilience to multipath effect.

2.1.3 Channel Estimation and Equalization

As discussed above, ultrasonic in-air communications are strongly affected by multipath and Doppler spread, leading to frequency selectivity and ISI that compromise the bit recovery operations at the receiver. The present framework implements channel estimation and equalization functionalities to estimate the channel impulse response (CIR) and mitigate the distortion produced by the channel.

Channel Estimation.

The communication system can utilize a training-based channel estimation approach that requires the presence of a training sequence known a priori in the transmitted packet. In particular, the system leverages the good-autocorrelation property of the synchronization preamble sequence, discussed in Section 2.1.2 above, to estimate the CIR. By correlating the output of the channel, i.e., the received signal, with the input, i.e., the known preamble sequence, an estimate of the time-domain CIR can be obtained.

Zero-Forcing Equalization.

The system can implement a linear equalization technique, zero-forcing (ZF) equalization, that aims to minimize the ISI signal distortion produced by the channel. A ZF equalizer is a finite-impulse-response (FIR) filter of order N that, for each input symbol, forces to zero the ISI components introduced by the 2N adjacent symbols. The filter taps are numerically calculated starting from an estimate of the CIR, which also accounts for the ISI effect.

2.1.4 Forward Error Correction

The system can include a forward error correction (FEC) functionality, based in some embodiments on Reed-Solomon (RS) codes. RS codes are linear, block error-correcting codes used in data storage and data transmission systems. A RS encoder takes k information symbols and adds t parity symbols to make an n symbol block. Therefore, there are t=n−k overhead symbols. On the other hand, a RS decoder is able to decode the received n-symbol block, and can correct up to t/2 data symbols that may contain potential errors due to the channel fluctuation or collisions with interfering packets. The RS coding rate can be defined as the ratio between the message length and the block length, i.e., k/n.

2.2 Data Link Layer

The data link layer provides a set of functionalities that allow multiple nodes to efficiently access a shared medium, i.e., a network configuration, multiple access protocols and PHY layer adaptation, under the challenges posed by an ultrasonic in-air channel, such as long propagation delays, among others, as discussed in Section 1 above.

2.2.1 Network Configuration

The system can internetwork wearable devices in master/slave (M/S) or peer-to-peer (P2P) configurations. Both configurations can coexist in the same network in hybrid configurations. For example, referring to FIG. 1, a master/slave configuration is shown by solid lines between the nodes and a peer-to-peer configuration is shown by dashed lines.

Master-Slave Configuration.

In the M/S configuration, one node takes the role of master, i.e., network coordinator, while the remaining nodes operate as slaves. In this scenario, the network control is concentrated on a master node, typically with higher resources available, e.g., processing, memory, power and connectivity. For example, an M/S configuration may be used in continuous monitoring systems where a master processing node 30, e.g., a smartphone, or a laptop, is used to fetch, analyze and display data collected by wearable sensors at nodes 20. Wireless or wired Internet connectivity can allow the master node to connect the wearable network with, for example, a medical center where a patient's data can be stored and analyzed remotely.

Peer-to-Peer Configuration.

In the P2P configuration, all the network wearable nodes 20 are treated as peers. This scenario suits, among others, applications that require distributed coordination among nodes for closed-feedback-loop monitoring and actuating tasks. For example, this may include a skin patch drug-delivery system where a drug pump can trigger a sensor for measurement, as well as where a sensor may trigger the drug pump for drug injection after a measurement.

2.2.2 Medium Access Control Protocols

The system can employ fully-functional multiple access protocols, such as, for example, polling, ALOHA and carrier sense multiple access (CSMA) with collision avoidance (CA), as well as primitive functions to implement custom protocols, e.g., idle listening, random backoff, or checksum-based error control mechanism.

Polling Protocol.

Polling is a deterministic access protocol for an M/S network configuration. In a polling scheme, the master node has complete control over channel access, while each slave node is granted access to the medium in a round-robin fashion.

ALOHA.

ALOHA is a random access protocol where nodes do not check whether the channel is busy or idle before transmitting. Nodes that want to transmit data simply access the channel and transmit the data. When collisions occur, nodes attempt retransmissions after a random time interval, i.e., backoff time.

Carrier Sense Multiple Access.

CSMA/CA is a multiple access technique based on carrier detection, which allows multiple nodes to share the channel by avoiding simultaneous transmissions, therefore avoiding collisions among transmitted packets. When a node wants to transmit a data packet, it first listens to the channel. If the channel is sensed as idle during a fixed time interval, the node transmits, otherwise waits for a backoff time before attempting a new transmission.

2.2.3 PHY Layer Adaptation

The system defines a set of cross-layer functionalities that enable real-time reconfiguration of PHY layer parameters from upper layers of the protocol stack, e.g., data link or network layer. By leveraging the flexibility of the software-defined architecture, upper layer protocols can reconfigure on-the-fly PHY layer parameters such as modulation, signal bandwidth and FEC coding rate, among others. Reconfiguration functionalities allow development of reactive or proactive control algorithms to adapt the underlying communication link to the channel variations or to upper layer protocol requirements.

2.3 Network Layer 2.3.1 IPv4 and IPv6 Support

The system can provide interoperability with the Internet by defining an adaptation layer that integrates IPv4 and IPv6 protocol support. The adaptation layer comprises a set of functionalities that interface the traditional IP network layer with the data link layer, by offering IP header compression and IP packet fragmentation functions optimized for ultrasonic wearable networks with long propagation delays that potentially prevent accurate timing of network protocols. For example, by leveraging cross-layer header information, the long IPv4 and IPv6 headers can be shortened to reduce network delay and energy consumption when exchanging small information packets.

2.3.2 Content-Centric Networking

The system can provide content-centric networking (CCN) functionalities that make the network content directly addressable and routable. Each sensor data or actuation command, i.e., each content object, is labeled with a name, and can be accessed through this name. Nodes can request content objects by broadcasting a request message. When a match is found, i.e., the content is found on a network node, a response message containing the requested content is sent back.

2.4 Application Layer 2.4.1 Reconfigurable and Modular Data Processing

The system adopts the idea of decomposing the data processing applications running in the sensor nodes into primitive blocks, and can offer real-time reconfigurability at the application layer. The sensing application comprises a sequence of basic operations that are executed on the sensor data to extract desired medical parameters. Real-time modular reconfiguration offers three main advantages. First, the network coordinator can wirelessly install new applications on sensor nodes at runtime, as needed. Based on this, resources are allocated only when the application is requested, thus reducing the processing and memory overhead due to static applications continuously running in background. Second, modular reconfiguration enables programmers to easily create new applications by arranging the primitive building blocks in the desired execution sequence. As a consequence, new medical parameters can be extracted from the raw data coming from a sensor, while maximizing code reusability. Finally, in case of template matching applications, e.g., ECG anomaly detection by matching ECG traces with known templates, adding or updating templates becomes simple with a reconfigurable application layer.

Defining new applications comprises specifying inputs, a chain of primitive blocks, and outputs. An input is the physical sensor that generates the data, e.g., accelerometer or electrocardiogram (ECG). An output can be either the local memory for storing a measured parameter, or a transmission for sending a measured parameter to another node. Outputs can be associated with triggering events, e.g., transmit a packet or store a measure if its value falls in a given range, or can be periodic. For each application, a sampling rate, i.e., how often to sample the input sensor data, and a sampling interval, i.e., how long to process the data for, is defined. The set of primitive blocks is divided into three main classes, filters, data operations, and detectors. Filters enable filtering the raw data to remove offsets, drift of the sensors and any other noise components coming from external sources. Data operations include common signal processing operations performed on sensor data, e.g., correlation with templates, and FFT, among others. Detectors allow measuring the desired parameters by detecting specific elements in the processed signal, e.g., peaks, patterns and time distances, among others.

2.4.2 Data Collection

The application layer can operate in two different modalities to exchange and collect data: fetch mode and push mode.

Fetch Mode.

Fetch mode is used when the application layer requires content from the network, and the node transmits a request mask to fetch this data. The node waits for a response from one or more nodes that possess the requested content. When a response is correctly received, if all the requested entities have been received the node goes back to the idle state.

Push Mode.

Push mode is used when sensed data needs to be pushed to another node, e.g., high glucose level in the blood, or when a node requires another node to accomplish some actuating operation, e.g., inject insulin or trigger a neurostimulation. In case of actuating commands, the push packet can contain further information about the required action, e.g., the quantity of insulin to inject or the pattern of the neurostimulation.

3. Prototypes

Two prototypes have been built that implement the framework discussed in Section 2 above. The first prototype is a wearable ultrasonic sensor node based on a custom hardware platform, referred to as a wearable node. The second prototype is a wearable ultrasonic coordinator based on an iOS commercial smartphone device, referred to as a wearable master.

3.1 Wearable Node Prototype 3.1.1 Hardware Design

FIG. 3 illustrates an embodiment of the hardware architecture of a wearable node 20. The core unit 60 includes a processing unit 40, e.g., microprocessor or microcontroller, a memory unit 62, e.g., RAM or flash memory, and digital-to-analog and analog-to-digital converters 42a, 42b. The core unit is in charge of sampling, processing and storing sensed data, and of orchestrating ultrasonic networking operations. Specifically, the processing unit executes the system functionalities discussed in Section 2. The communication unit 46 enables ultrasonic wireless connectivity by embedding power and low noise amplifiers 54, 52, and air-coupled ultrasonic transducers 48. A power unit 70 can include a battery 72 to power the wearable node. An optional wireless energy transfer unit 74 can be installed to leverage ultrasonic power transmission to wirelessly charge the node's battery. A sensing and/or actuating unit 80 can incorporate several sensors and actuators according to the specific application design, e.g., accelerometers, ECG, drug pumps and neurostimulators, among others.

Figure 4:
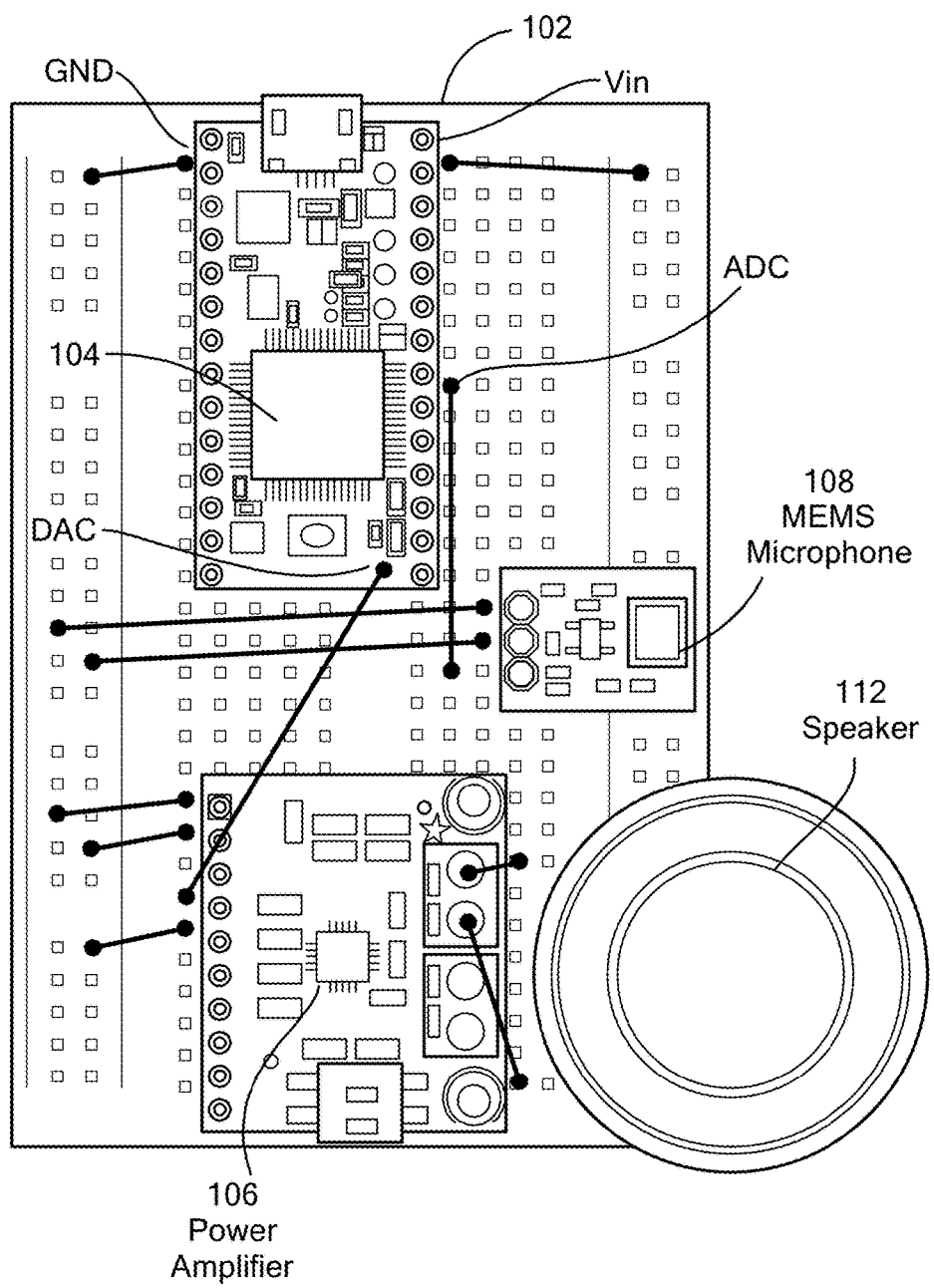
FIG. 4 is an illustration of an ultrasonic communication system prototype.

The architecture in FIG. 3 of the prototype has been implemented based on the Teensy 3.1 platform, a microcontroller development board. The wearable node offers near-ultrasonic capability, by using commercial off-the-shelf (COTS) audio speakers and microphones as air-coupled ultrasonic transducers. FIG. 4 shows the basic circuit design of the wearable node prototype on a solderless breadboard 102. The prototype includes a Teensy 3.1, i.e., the core unit 104, a power amplifier 106, a microphone 108, and small audio speaker 112, i.e., the communication unit. A lithium ion polymer battery, not included in the figure, is connected to the bus strip of the breadboard to power the electronic components. It will be appreciated that these prototype hardware components can be embedded in a customized PCB.

Teensy 3.1.

Teensy 3.1 is a small-footprint, i.e., about 3.5×1.8 cm, breadboard-friendly and inexpensive development board, based on a 32 bit ARM Cortex-M4. It comes with 64K of RAM, 256K of Flash, 12 bit DAC, dual ADC, and USB connectivity. Teensy 3.1 can be programmed in C and C++ using Teensyduino, a customized version of the Arduino integrated development environment (IDE), and supports many of the code libraries designed for Arduino and others specifically designed for Teensy, e.g., an audio library, among others. Teensy 3.1 can be powered via USB, or through external batteries connected to the $V_{in}$ and GND pins.

The Teensy 3.1 was selected among other available COTS platforms such as USRP N210, Raspberry Pi, or Arduino Uno. Compared to USRP N210 and Raspberry Pi, where software operations are executed on top of an operating system running on external or internal microprocessor, Teensy 3.1 and Arduino Uno are designed around a low-power micro-controller that provides low-level control of the hardware peripherals. Microcontroller-based platforms offer higher hardware flexibility and computational efficiency that suit the design requirements of wireless wearable devices. Finally, Teensy 3.1 was selected over Arduino Uno because of the more powerful microcontroller and larger available memory that can support high audio sampling rates compatible with the near-ultrasonic communication range, e.g., 44.1 kHz for acoustic frequency up to 22 kHz. Teensy 3.1 still supports the Arduino libraries that can significantly ease the prototyping process of the wearable node.

Power Amplifier.

The wearable node includes a small and efficient class D audio amplifier able to deliver a maximum of 1 W into 4 ohm impedance speakers, with a voltage supply of 3.3 V DC, and efficiency up to 80%. The amplifier consumes less than 2 mA of current when quiescent and less than 2 μA in standby mode. In FIG. 4, the right channel of the power amplifier is connected to Teensy via the DAC pin, and to the speakers via the 3.5 mm screw-terminal blocks. The $V_{cc}$ and GND pins are connected to the bus strip to power the device.

Microphone.

The input of the wearable node is a tiny breakout board that embeds an ADMP401 MEMs microphone and a low-noise amplifier. The ADMP401 offers a mostly flat bandwidth, i.e., −3 dB roll off, between 100 Hz and 15 kHz, omnidirectional sensitivity pattern, and requires a supply voltage between 1.5 V and 3.3 V DC. Although a microphone with larger bandwidth would perform better, the selected solution is desirable because of the COTS breakout board package that eases prototyping. Moreover, even though with lower sensitivity, the ADMP401 can still detect higher frequency acoustic waves up to 22 kHz. The microphone is connected to one of the analog pins (ADC) available in Teensy 3.1, and is powered by connecting the $V_{cc}$ and GND pins to the bus strip.

Audio Speaker.

The output of the wearable remote is a small and compact COTS speaker, Dayton Audio CE28A-4R, with 4 ohm impedance, 4 W maximum output power supported, and flat frequency response between 100 Hz and 15 kHz. The speaker is connected to the power amplifier using 3.5 mm screw-terminal blocks.

It will be appreciated that the hardware architecture can be implemented with other hardware components than those describe in conjunction with the prototype of FIG. 4.

3.1.2 Software Architecture

Figure 5:
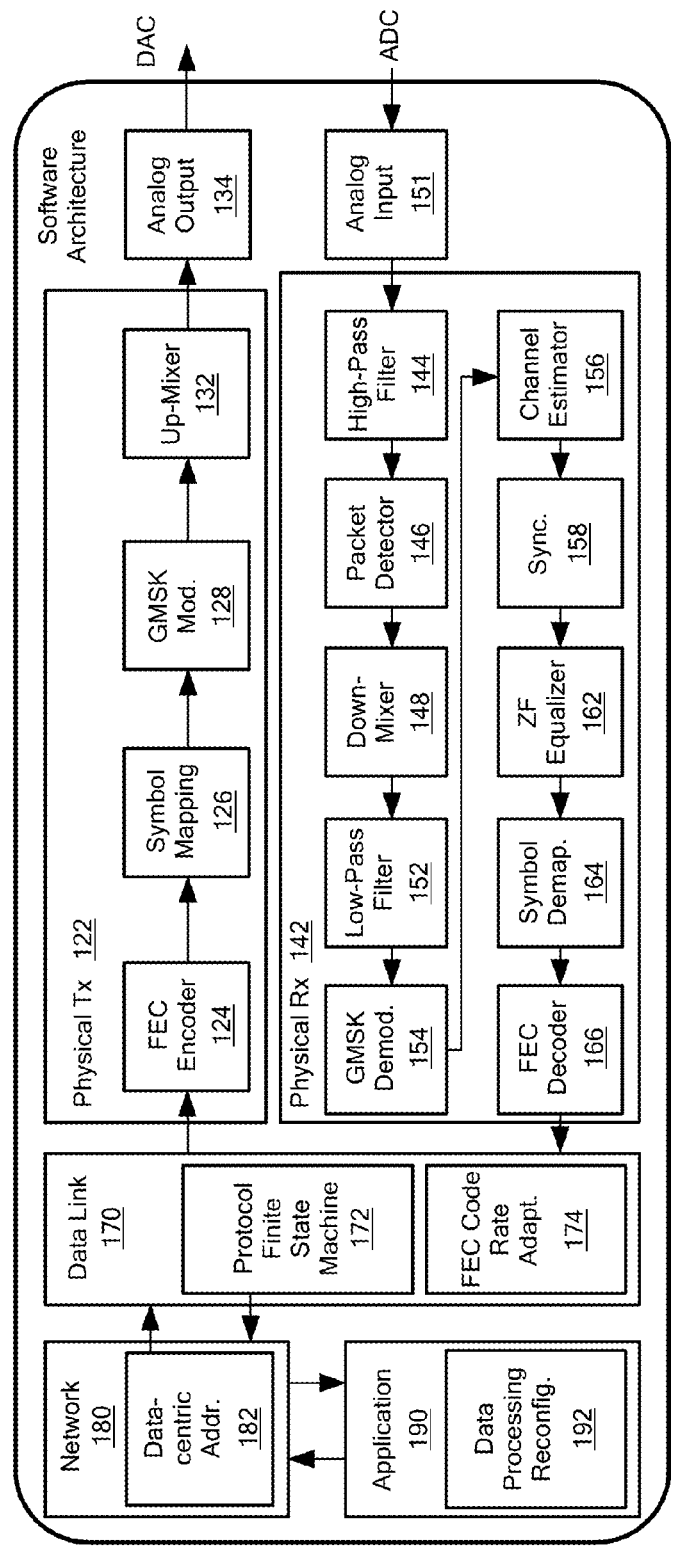
FIG. 5 is a schematic block diagram illustrating a software architecture embodiment of an ultrasonic communication system.

The system framework was implemented in Teensy 3.1 to enable ultrasonic wireless connectivity and networking on the wearable node hardware prototype. FIG. 5 shows a block diagram of an embodiment of a wearable node software architecture that includes (i) narrowband GMSK transceiver with synchronization, channel estimation, equalization, and FEC functionalities at the PHY layer, (ii) polling and ALOHA multiple access protocol with FEC coding rate reactive adaptation at the data link layer, (iii) content-centric addressing at the network layer, and (iv) data processing reconfiguration with fetch and push support at the application layer.

The wearable node functionalities were implemented using Teensyduino, an add-on for the Arduino IDE, leveraging many of the code libraries available for the Arduino platform. Since ultrasonic waves are sound waves at higher frequencies, the PHY layer signal processing was based on the audio library specifically designed for Teensy 3.1. The Teensy audio library includes a set of objects that enable recording, processing, and playback of audio sampled at 44.1 kHz. Objects instantiate specific audio functionalities, e.g., a waveform synthesizer and finite-impulse-response (FIR) filters, while new functionalities can be enabled by creating new objects. A cascade of objects forms a processing chain that performs a set of operations on inputs to produce a desired output. Each object in the chain operates in pipeline on chunks of 128 audio samples, which correspond to 2.9 ms of audio. To guarantee audio continuity, each block must execute its processing operation within 2.9 ms.

In the wearable node implementation, custom-made objects were built that implement specific signal processing operations. Since some computationally expensive operations exceed the audio library time constraints of 2.9 ms, these were implemented outside of the audio library. These are referred to as off-the-chain objects.

Physical Tx.

The first object of the PHY layer Tx chain 122 is the FEC Encoder 124. Here, each data packet coming from the data link layer is coded, as discussed in Section 2.1.4, and overhead symbols are appended to the original packet, selecting n=255 symbols and parity symbols t to achieve different coding rates, e.g., 1/2, and 2/3, among others. Because of the computation complexity of RS coding, the FEC Encoder is implemented as an off-the-chain object. The coded packet is then passed to the Symbol Mapping object 126 that inputs the audio stream in the processing chain. Here, the coded packet is serialized, i.e., converted into a stream of bits, differentially encoded, and transformed into a non-return-to-zero (NRZ) signal. The NRZ signal is then GMSK modulated by the GMSK Modulator object 128 and up-converted to the carrier frequency by the Up-Mixer object 132. The modulated and up-converted waveforms are passed to the Audio Output object 134, i.e., a system API that interfaces the system with the embedded DAC (42*a*, FIG. 3), digital-to-analog converted and transmitted through the power amplifier (54, FIG. 3) and audio speaker (48, FIG. 3).

Physical Rx.

The received acoustic signal is converted into an electrical signal by the MEMS microphone. The signal is amplified by the LNA (52, FIG. 3), and analog-to-digital converted by the Teensy 3.1 ADC at 44.1 kHz. The Audio Input object 151 is a system API that interfaces the system with the embedded Teensy 3.1 ADC (see also 42*b*, FIG. 3), and inputs the audio stream into the PHY layer Rx chain 142. The received digital signal is first high-pass filtered by the High-pass Filter object 144 to eliminate low-frequency noise and interference, i.e., external human voice and ambient noise. The Packet Detector 146 processes the input signal to detect incoming packets using an energy-based approach to check whether there is energy at the expected carrier frequency. The incoming packet is then down-converted by the Down Mixer 148, i.e., converted into a complex in-phase/quadrature baseband signal, and low-pass filtered at filter 152 to eliminate undesired higher-frequency harmonics introduced by the nonlinearity of the down-conversion operation.

Channel estimation, synchronization and equalization operations normally follow down-conversion and are applied to the complex baseband signal. However, these operations are computationally expensive, and their execution exceeds the audio library time constraints of 2.9 ms. To overcome this limitation, the complex baseband signal is first demodulated in the GMSK Demodulator object 154 to extract the phase variation that carries the coded information bits. Then, the computationally expensive operations are executed off-the-chain. The Channel Estimator object 156 estimates the CIR using the packet preamble as training sequence, as discussed in Section 2.1.3, while the Synchronizer object 158 attempts to achieve fine synchronization through the PN-based mode discussed in Section 2.1.2. The ZF Equalizer object 162 filters the input for ISI recovery, as discussed in Section 2.1.3. The equalized symbols are demapped at demapper 164 into a bitstream, collected into a packet structure, and passed to the FEC Decoder object 166. Here, FEC decoding operations attempt to correct potential bit errors, as discussed in Section 2.1.4. Finally, the error-corrected packet is passed to the data link layer 170.

Data Link Layer.

One embodiment of the wearable node data link layer 170 is implemented in a Finite State Machine (FSM) block 172 that can include two of the MAC protocols discussed in Section 2.2, polling and ALOHA. Polling can be exclusively used in M/S configuration, while ALOHA works in both M/S and P2P configurations. The wearable remote data link layer also implements a PHY layer adaptation 174 to optimally select the FEC coding rate that minimizes the number of retransmissions. The MAC protocol FSM 172 is also in charge of coordinating the PHY layer receiving and transmitting operations. During packet transmission, the MAC FSM collects data from upper layer protocols and creates the data-link-layer packet. The packet starts after a preamble that enables coarse and fine synchronizations and allows the receiver to detect an incoming packet and identify the exact packet start time. The packet payload is followed by a 16-bit checksum that is used at the receiver to identify if the packet has been correctly received. The packet is then forwarded to the PHY layer Tx chain 122, where it is encoded in a digital waveform before being transmitted. At the receiver side, the MAC FSM detects the received packet based on information coming from the Packet Detector block 146 and triggers the PHY layer 142 to start processing the received waveform. The MAC FSM is also in charge of checking the packet checksum, and forwarding the received data to the upper layer.

Network Layer.

One embodiment of a wearable node network layer 180 can implement the content-centric addressing scheme 182 discussed in Section 2.3. Each content object can be mapped into a binary mask, where it is represented by the bit position in the mask, e.g., '0001' for the "heart rate" content, '0010' for the "footsteps" content and '0100'. The binary mask has variable length and can be adjusted to match the number of entities available in the network.

In an M/S configuration, a node joining the network is first paired with the master node. The master maps the content available in the new node into the binary mask, and broadcasts the updated mapping to all the nodes in the network. Each node builds a local mask based on the entities that it possesses. To request an entity, the master broadcasts a request message containing a request mask with '1' set in the position mapped to the desired content. For example, to retrieve heart rate and footsteps content, the '0011' request mask is broadcasted in the network. Slave nodes compare the request mask to their local masks, and forward the matching contents, if any. In a P2P configuration, the pairing operation is replaced by a discovery operation, and the binary mask is maintained distributively in the network. When a new node joins the network, it requests the current mask mapping from neighbor peer nodes, updates it with the contents it holds, and then broadcasts the updated mapping.

Application Layer.

In one embodiment, a wearable node application layer 190 can implement real-time modular reconfiguration functionalities 192, as discussed in Section 2.4, and can support both fetch and push data collection operations. Following is a list of some examples of the primitive blocks implemented in this prototype:

fir_filter: a FIR filter that accepts parameters defining filter specifications, i.e., cutoff frequencies.

find_peaks: finds peaks in a 1-dimensional data sequence given a threshold value.

find_next_extr: returns the next local extremum, i.e., maximum or minimum, after or before a peak.

calculate_distance: calculates distances between time instants, e.g., peak-to-peak.

average and std, return the average and standard deviation of the input data.

count_events: implements a counter of events, e.g., how many times a value exceed a given threshold.

Based on this modular approach, applications can be represented by chains of binary sequences, i.e., keys. Each primitive function is mapped to a binary key. A concatenation of keys represents a concatenation of operations, and therefore represents an application. The application is encapsulated into reconfiguration packets and transmitted over-the-air. The receiving node extracts the binary keys, and feeds these into an FSM where each state represents a primitive block function. By parsing the consecutive function keys, the FSM transitions from state to state, processing inputs and producing outputs. Inputs and outputs of each function are mapped to binary keys as well, and are implemented in a C-struct output_struc that contains a pointer to an array, and a binary key variable. The input and output keys allow parametrically passing data between functions. Absolute inputs, those coming from the sensing hardware, are also represented by binary keys, and can usually be fed to the first block of the application chain. Finally, function parameters can be serialized and also passed in the form of binary strings.

As a proof-of-concept, some applications were developed based on the primitives discussed above.

Electrocardiogram (ECG) Processing.

Figure 6:
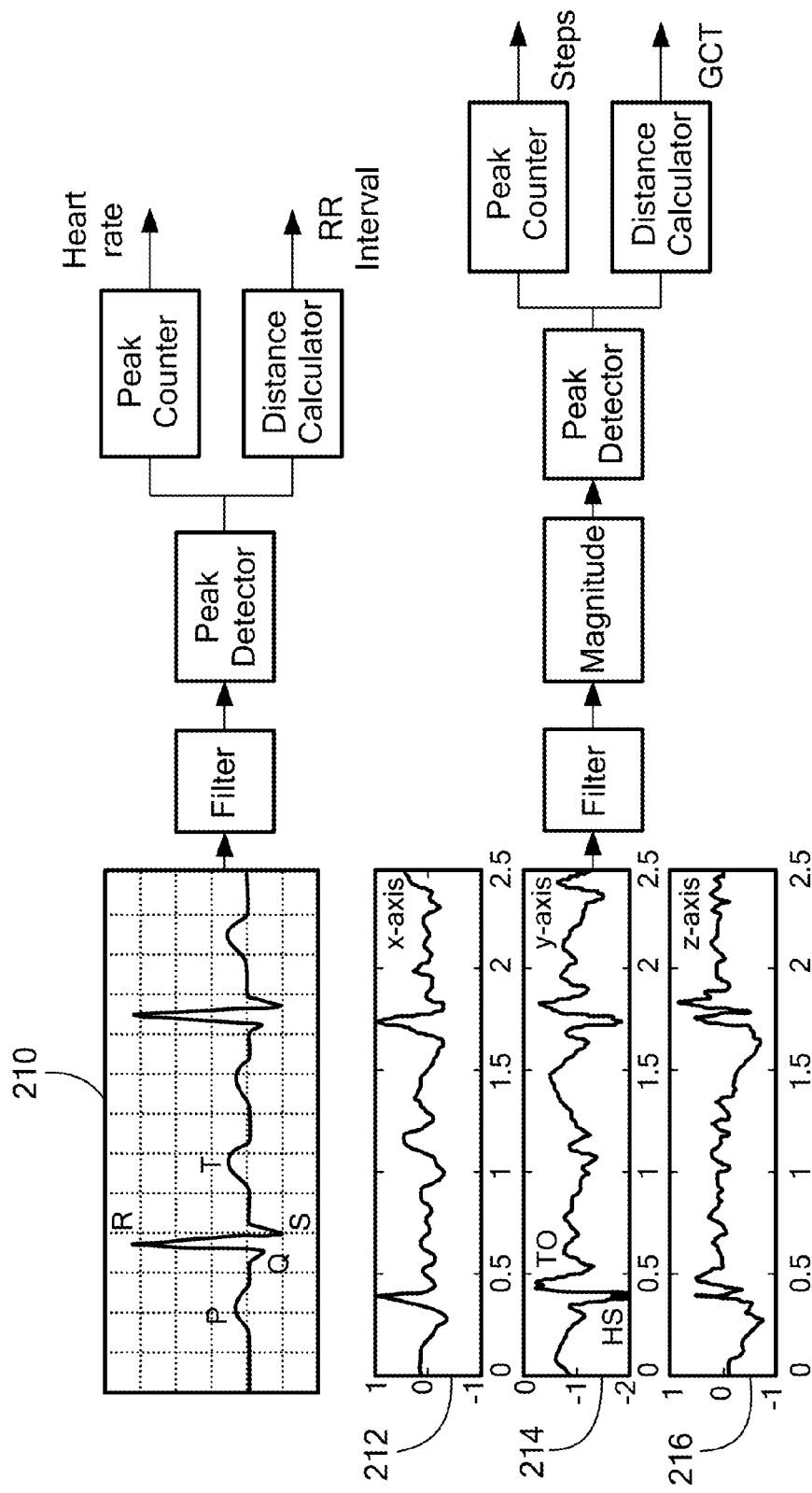
FIG. 6 is a schematic illustration of primitive blocks of a heart rate and RR interval monitor (top) and footstep and GDT monitor (bottom) using an ultrasonic communication system.

Consider a single-electrode ECG signal. FIG. 6 shows a template signal 210 with five labelled characteristic waveforms, i.e., P, Q, R, S and T, that correspond to three electrical events during one heartbeat, i.e., atrial contraction (P), ventricular contraction (QRS) and ventricular recovery (T). The first application measures the heart rate in beat-per-minute [bpm]. This is done following two different approaches. The first approach, here R method, counts the number of peaks, R waves, in a 6-second trace and multiplies the result by 10. The second approach, here RR method, finds the number of heartbeats per second by inverting the average of the RR interval duration, i.e., distance between two consecutive R waveforms in the trace, and multiplies this by 60. This approach has higher complexity with respect to the R-method, but results in higher resolution, i.e., 1 bpm against 10 bpm of the R method. The second application measures average and standard deviations of temporal separation between electrical events in the ECG. For example, the distance between peaks, i.e., R waves gives the RR interval duration. The mean and standard deviation of the RR interval give important information about potential heart arrhythmias or other malfunctioning. FIG. 6 (top) shows the simplified primitive block sequences of the R method heart rate detector and the RR interval monitor applications.

Accelerometer Processing.

The accelerometer trace in FIG. 6 shows the frontal acceleration on the x-axis 212, the vertical acceleration on the y-axis 214, and the lateral acceleration on the z-axis 216. Two main events are labeled in the y-axis that occur during a single step, i.e., heel strikes (HSs) and toe-off (TO), that correspond to the instants at which the foot touches the ground, and the instants at which the foot leaves the ground, respectively. Based on this, the first application calculates the magnitude of the acceleration from the three-axis components, low-pass filters it to remove high frequency noise, and counts the number of peaks in the resulting signal, i.e., the number of HSs. The peaks within a time interval represent the number of footsteps performed by the patient. The second application measures average distances between events in the accelerometer trace. For example, the distance between non-consecutive peaks in the acceleration magnitude gives the gait cycle time (GCT), i.e., time between consecutive HSs on the same foot. GCT offers a measure of the motor degradation of patients affected by Parkinson disease. FIG. 6 (bottom) shows the simplified primitive block sequences of the footstep counter and the GCT monitor applications.

3.2 Wearable Master Prototype

Figure 7:
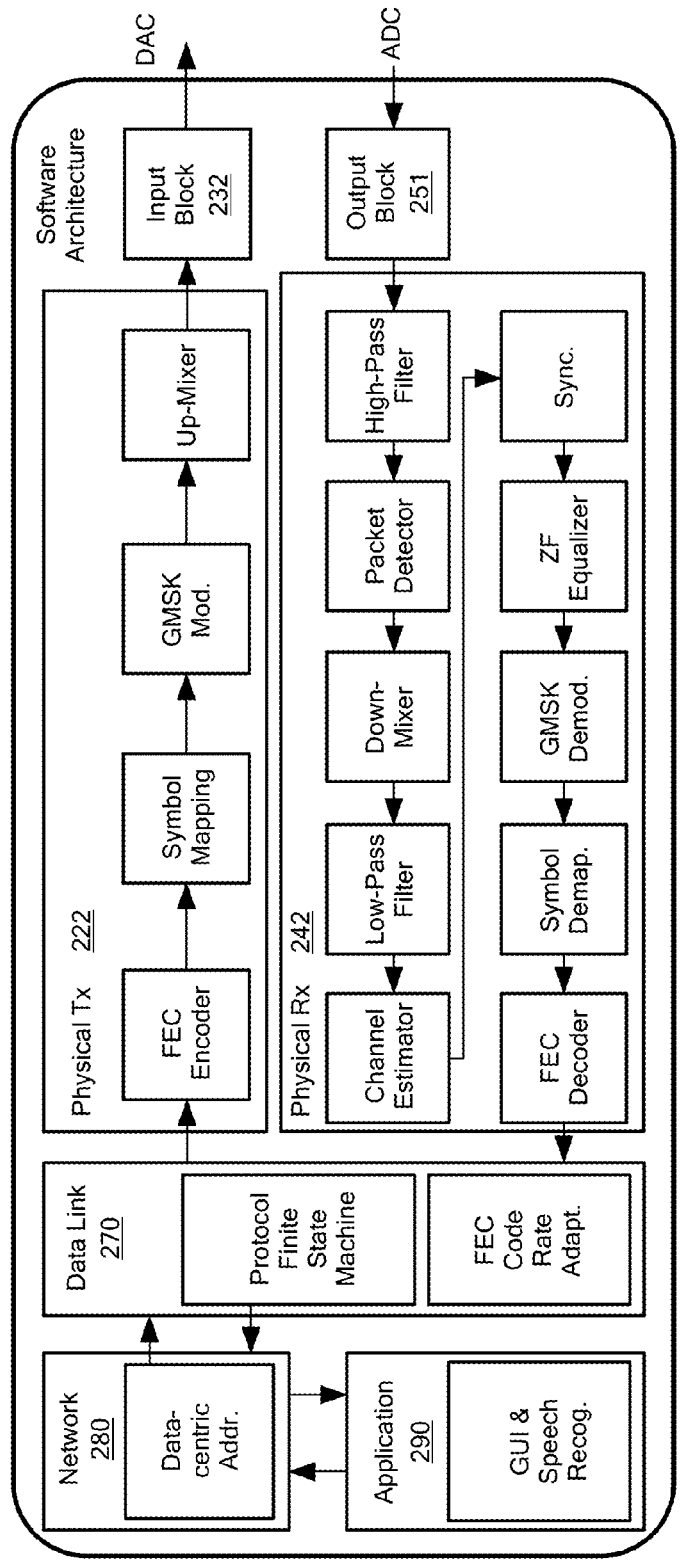
FIG. 7 is a schematic block diagram illustrating a software architecture embodiment of an ultrasonic communication system.

An embodiment of a wearable master node prototype was implemented on the iOS 8 platform for Apple iPhone smartphones. The prototype comprises an app running on an iPhone smartphone that implements the system multi-layer functionalities. FIG. 7 shows an embodiment of the software architecture of the wearable master prototype that includes (i) narrowband GMSK transceiver with synchronization, channel estimation, equalization, and FEC functionalities at the PHY layer, (ii) polling and ALOHA multiple access protocol with FEC coding rate reactive adaptation at the data link layer, (iii) content-centric networking at the network layer, and (iv) a graphic user interface (GUI) and speech recognition functionalities at the application layer that allow users to interact with the wearable network.

The iOS prototype can communicate wirelessly with the wearable nodes through an ultrasonic narrowband GMSK link, using the phone's embedded microphone and speaker. The software prototype was developed in Objective-C programming language using Xcode 6 integrated development environment (IDE), and leveraging the Xcode storyboard feature for developing the graphic user interface (GUI). Also used were (i) the vDSP library of the iOS Accelerate framework that implements digital signal processing (DSP) operations, (ii) Novocaine, a high performance audio library that enables record/play audio functionalities, and (iii) wit.ai framework that offers speech recognition services.

vDSP Library.

The vDSP library is part of the Accelerate framework available in iOS, and provides several DSP functionalities including vector and matrix arithmetic, Fourier transforms, convolution and correlation operations between real or complex data types. The vDSP functionalities can be leveraged to perform arithmetic operations and correlations on real and complex vectors in the PHY layer.

Novocaine.

Novocaine is a high performance audio processing library for iOS. Novocaine hides all the low-level audio implementation details, giving simple block-based callbacks that are called when audio comes in, and when audio needs to go out. Specifically, a Novocaine object, i.e., the Audio Manager, offers InputBlock and OutputBlock callbacks, inside which the DSP code can simply be placed for processing input and output data.

Wit.ai Framework.

Wit.ai provides natural language processing in the form of multi-platform APIs, which are used to integrate voice command in the system. Wit.ai allows developers to create commands, and to match these commands with intents. A command is what the user would say to trigger an operation, while the intent represents the operation itself. Voice commands are sent to the wit.ai server, and the intent with maximum confidence is returned as a response. Since wit.ai requires Internet connectivity to submit a request and receive a response, voice commands are available only through the wearable master with Internet connectivity. However, a lightweight embeddable version of wit.ai can be provided to make it possible to address voice commands directly to the wearable nodes.

PHY Layer Tx/Rx.

The PHY layer Tx 222 and Rx 242 are implemented in two classes named PHYLayerTx and PHYLayerRx, respectively. Here, the Novocaine Audio Manager triggers the InputBlock 232 and OutputBlock 251 callbacks to record and play audio, and the vDSP functions process the input and output data. At the transmitter, the PHYLayerTx class gets the data from the data link layer 270, generates the GMSK waveform, and then passes it to the Audio Manager. The latter transmits the GMSK waveform through the speaker. At the receiver, the operations in PHYLayerRx match those implemented in the wearable node PHY layer 242, discussed in Section 3.1.2 (see also FIG. 3). Because of the less stringent memory and processing constraints of the iOS platform, here the packet can be entirely stored in memory after being detected, and decoded right after. Moreover, channel estimation, synchronization and equalization operations follow the down-conversion, and are applied to the complex baseband signal.

Data Link and Network Layer.

The wearable master data link layer 270 can implement polling and ALOHA MAC protocols, as well as FEC coding rate adaptation. The MAC functionalities can be implemented in a class named MACLayer, where a FSM implements the MAC protocol operations. The wearable master network layer 280 can implement the same content-centric addressing scheme as in the wearable node prototype, with the exception that here the centralized mapping functionalities are also implemented.

Application Layer.

Figure 8:
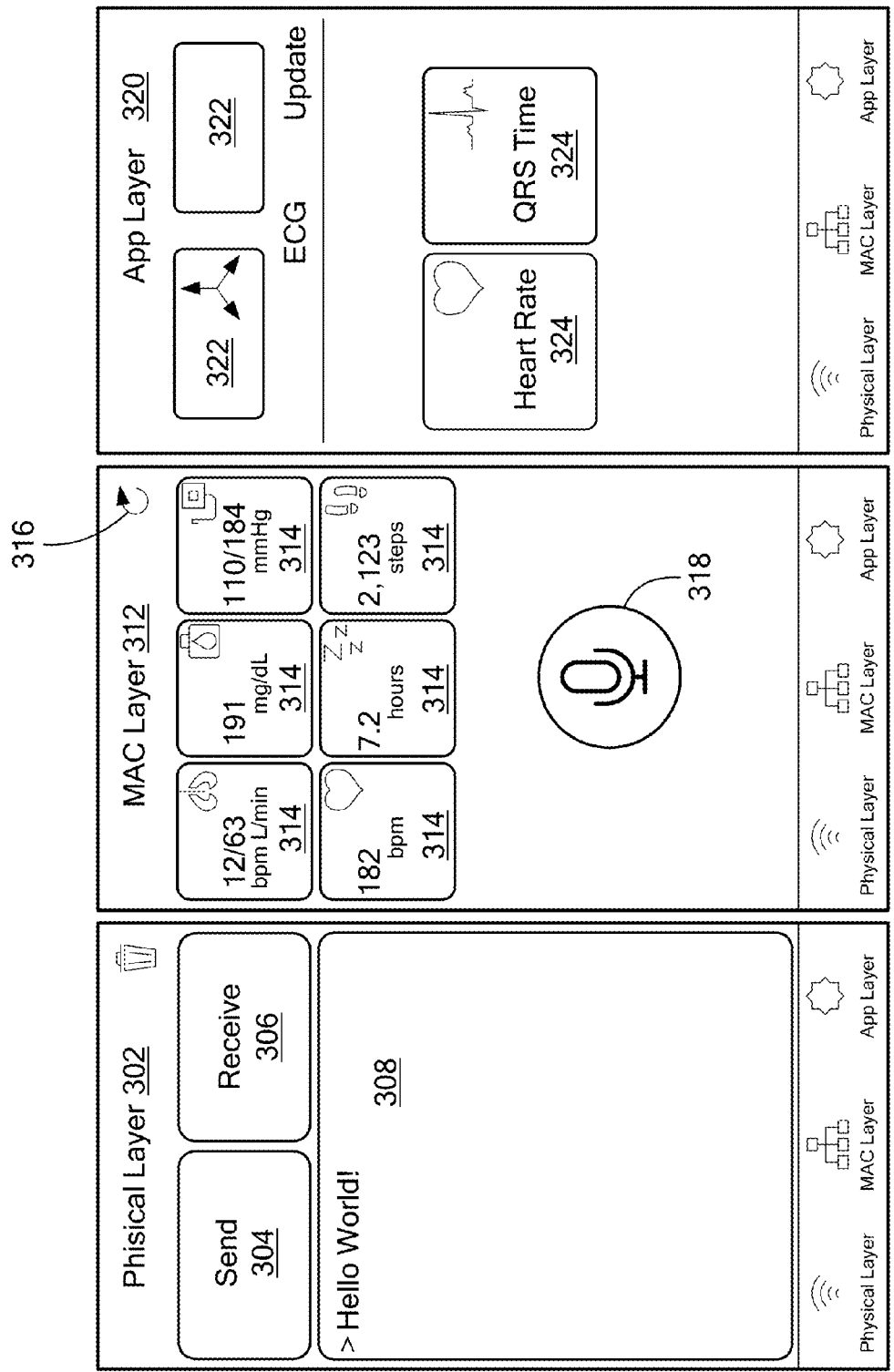
FIG. 8 is a schematic illustration of an embodiment of a graphical user interface for a physical layer (left), a MAC layer (center), and an application layer (right)

The wearable master application layer 290 can comprise a graphical user interface (GUI) and a set of wit.ai commands that allow interaction with the system multi-layer functionalities. In one embodiment, the GUI's principal element is a three-tab TabViewController class. The first tab 302, shown in FIG. 8 (left), contains a PHYViewController object. It inherits from UIViewController, i.e., a basic view controller in iOS, and is implemented for testing the PHY layer performance. PHYViewController accommodates two UIButtons 304, 306 that allow transmitting and receiving random data, and a console-like UITextView 308 that displays the transmitted packets, and the BER information of the received ones. The second tab 312 contains a MACViewController object that inherits from UIViewController and allows the user to test the MAC Layer functionalities by requesting, receiving and visualizing sensed data coming from the deployed wearable nodes. The MACViewController embeds a UICollectionView, a collection of objects 314 that represent the sensed data. In FIG. 8 (center) six objects 314 in the collection are shown, which are associated with the number of footsteps, the number of sleep hours, the heart rate, the breath rate and the respiratory minute volume, the glucose level in the blood and the diastolic/systolic blood pressure. A UIBarButtonItem refresh object 316 allows fetching all the monitored data. A WITMicButton 318, defined in the wit.ai framework, enables voice command processing. The current implementation supports several vocal commands that allow to fetch any of the monitored medical data, e.g., "measure my blood pressure", or "for how long did I sleep last night?", among others. The third tab 320 contains an APPViewController object that gives access to application layer reconfiguration functionalities discussed in Section 2.4. In the APPViewController, the applications are grouped based on the sensing unit that provides the required input data, e.g., accelerometer and ECG. Each UIButton 322 represents a group of applications, and it gives access to a PopViewController object that shows the available applications 324 in that group. Users can select which application to run on the wearable node. For example, FIG. 8 (right) shows how a user can select to install heart rate or RR interval monitor on wearable remotes equipped with ECG.

4. Performance Evaluation

The feasibility of ultrasonic communications for wearable devices is demonstrated through testbed experiments, and the performance of the prototypes discussed in Section 3 are evaluated. First, the physical layer performance of the prototypes is evaluated in terms of BER as a function of (i) the signal-to-noise ratio (SNR) at the receiver, and of (ii) FEC coding rate. Then, it is shown how the system MAC protocols allow network nodes to coexist while enabling users to efficiently access the sensed medical parameters. Finally, the reconfigurable data processing of the system is leveraged to install and run three applications built using the set of primitive blocks. The three applications are evaluated in terms of processing accuracy, i.e., the displacement between the obtained outputs and the expected ones.

4.1 PHY Layer Performance

Experiment Setup.

Figure 9:
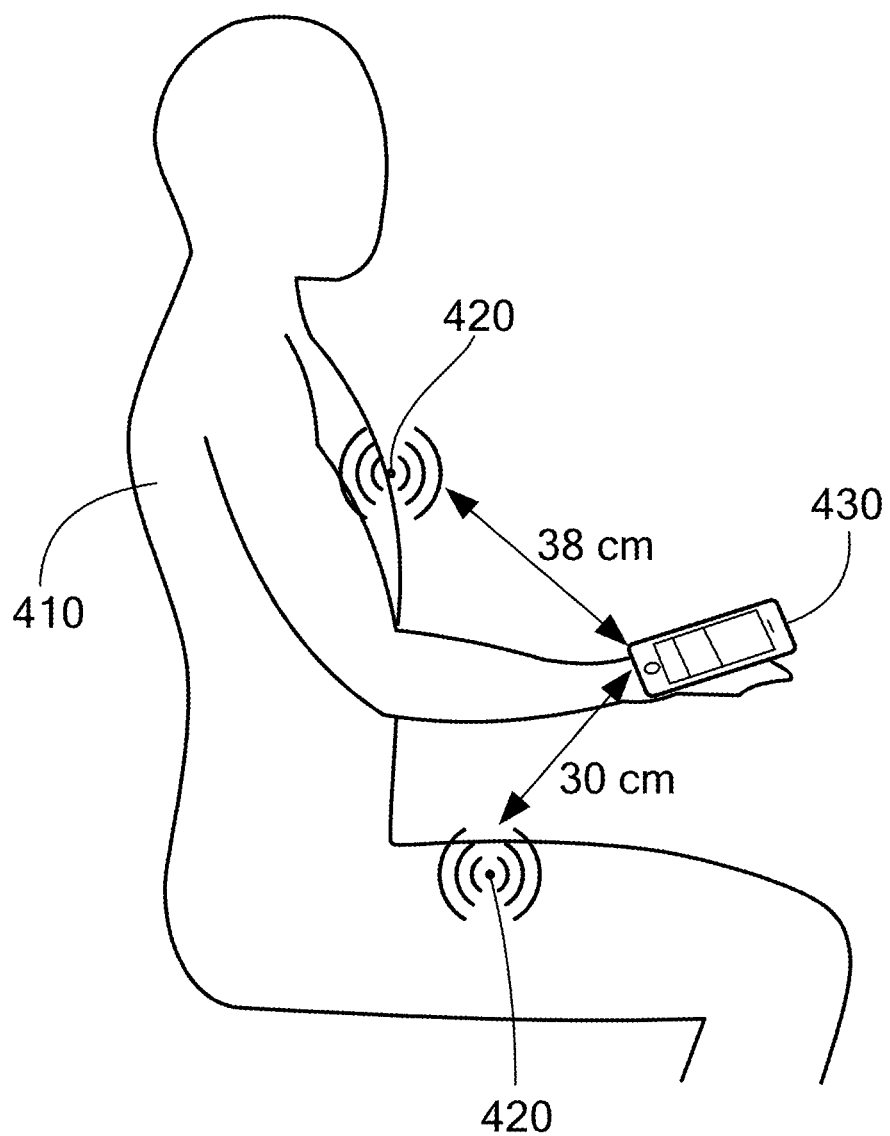
FIG. 9 is a schematic illustration of a near-line-of-sight (nLOS) experimental setup.
Figure 10:
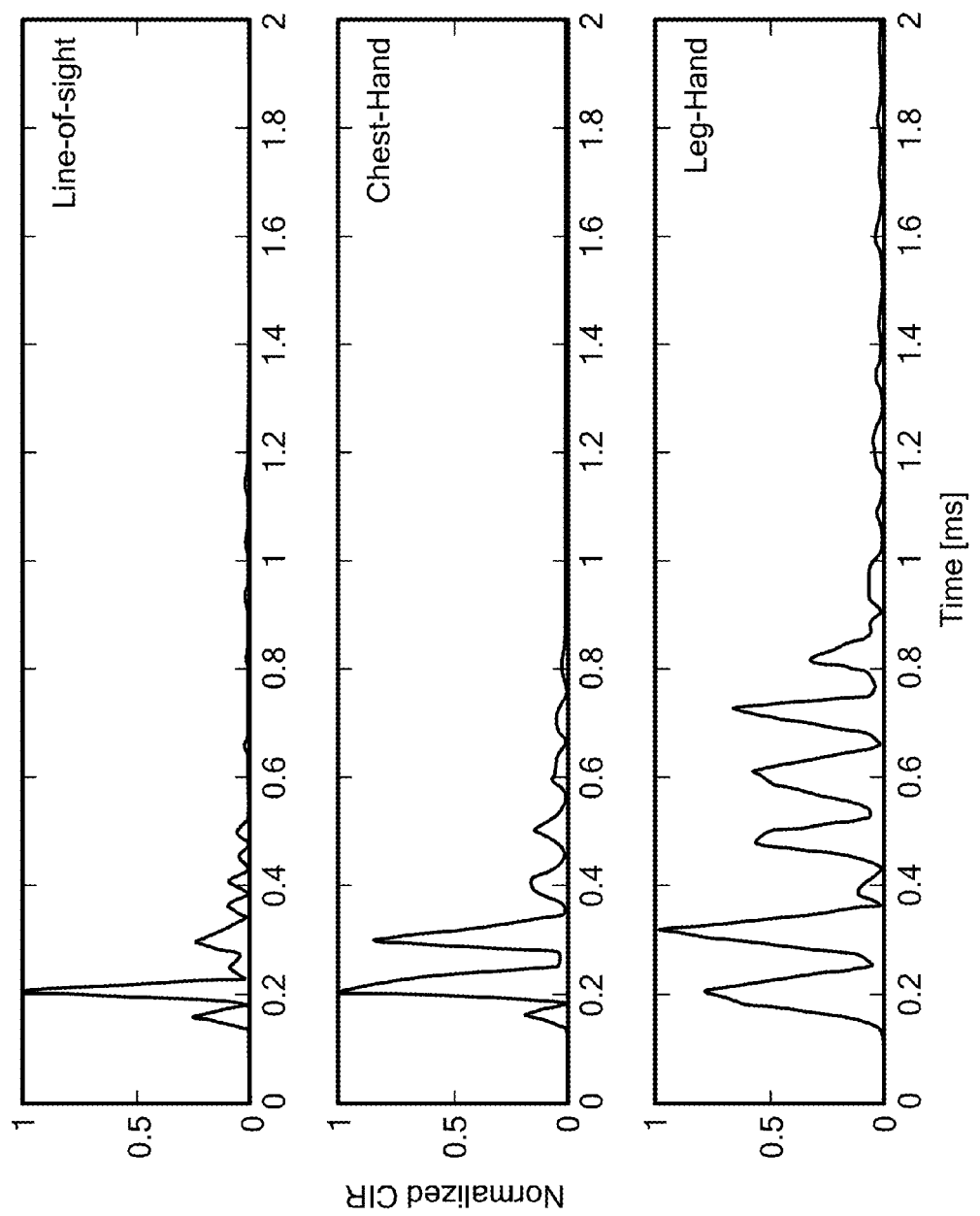
FIG. 10 is a graph of ultrasonic in-air CIR for line-of sight (LOS) (top), chest-hand nLOS (center), and leg-hand nLOS (bottom)

The experiment setup consists of a wearable node communicating bidirectionally with a wearable master in two different scenarios, line-of-sight (LOS) and near-line-of-sight (nLOS). In the LOS scenario the two devices are aligned, 50 cm apart, without obstacles in between, so as to minimize reflections and scattering. In the nLOS scenario, the wearable nodes 420 are located along the body 410 of a user, on the chest and on the right leg, as shown in FIG. 9. The wearable master node 430, located at the smartphone, is held in the user's right hand. Under this setup, objects within the propagation area cause reflections and scattering that introduce ISI and degrade the communication performance. FIG. 10 shows the uplink CIRs of the three scenarios discussed above. It can be observed that, in the LOS scenario, the CIR contains a single dominant component. In the nLOS scenario, because of the multipath, there are multiple components that contribute to ISI distortion at the receiver. In particular, in the chest-hand setup, the CIR clearly presents a second path, most likely because of a reflection from the user's hand, while in the leg-hand setup up to 6 paths can be counted, most likely caused by multiple reflections from the user's trunk and hand. The coherence bandwidth in these three scenarios is approximately 21 kHz, 14 kHz, and 6 kHz, respectively.

For each BER measurement up to 600 packets of 32 bytes, i.e., approximately 256 kilobits, are transmitted containing pseudorandom-generated raw data. The experiment was performed in an indoor room where the temperature was about 21° C. and the relative humidity was around 30%. The physical layer was configured such that each GMSK symbol is represented by 16 samples. The sample rate is set to 44.1 kHz as required by the audio hardware in use. Based on this, the raw physical layer data rate, obtained as the ratio between sample rate and sample per symbol, is approximately 2.76 kbit/s. The GMSK BT product is fixed to 0.7, which represents a good tradeoff between ISI distortion and spectral efficiency. The resulting signal bandwidth is of about 2 kHz, which is lower than the coherence bandwidth of the three experimental setups, thus complying with the definition of a narrowband transmission scheme. The central frequency is set to 18 kHz, which, while still in the audible frequency range, represents a good tradeoff between low audibility, fair propagation efficiency, and fair acoustic generation and detection with the COTS microphone and speaker in use. Specifically, it was found that 18 kHz is the highest frequency, given the spectral response of microphones and speakers in use, for which highly reliable communications could be obtained, i.e., relatively low BER, in the range of distances of interest, i.e., up to 1 m. At the same time, the signal transmission is almost inaudible by the user wearing the device. A 64-bit PN-sequence is used as preamble for synchronization and channel estimation purposes.

BER Performance in LOS.

Figure 11:
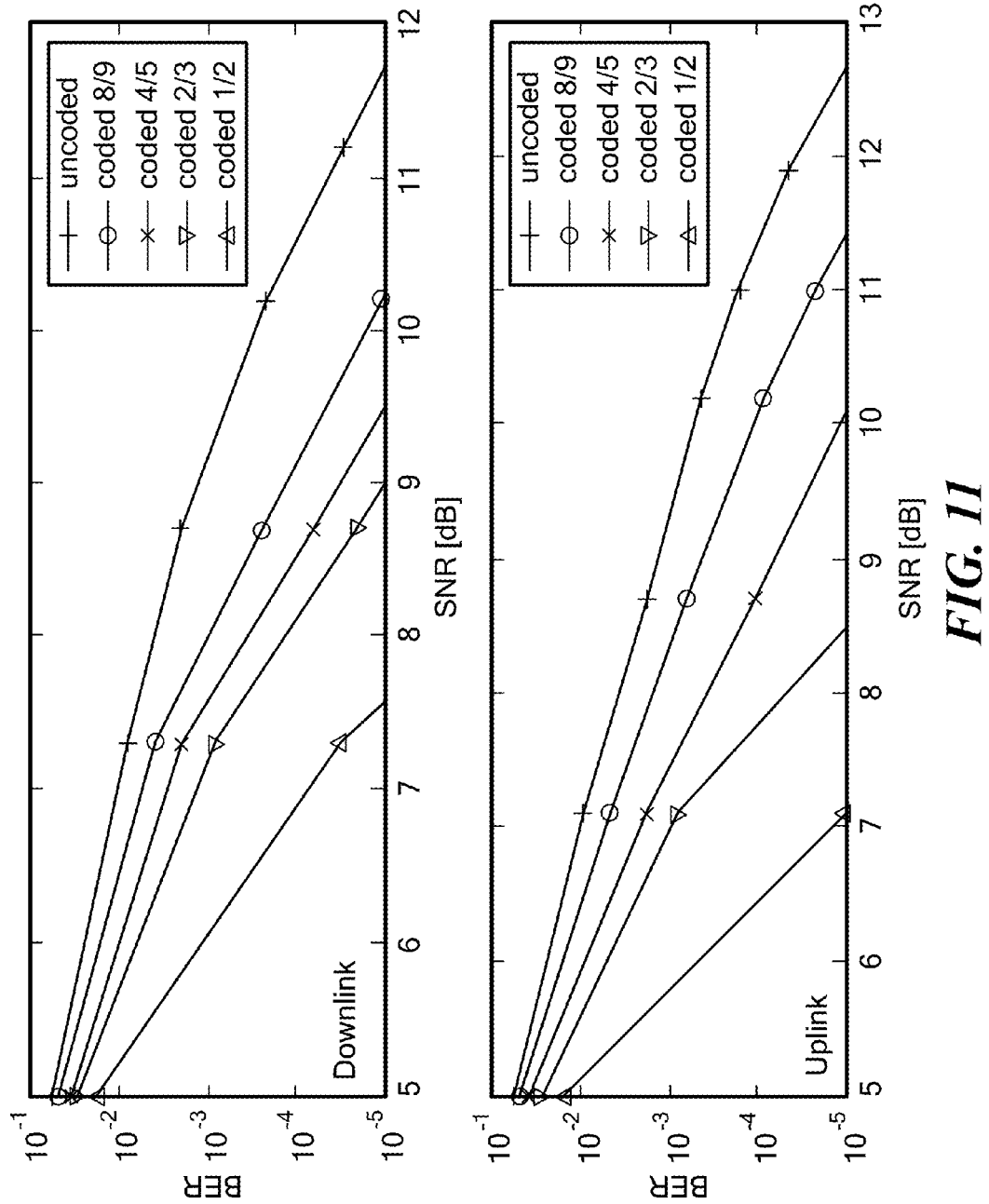
FIG. 11 is a graph of bit error rate (BER) of a downlink (top) and uplink (bottom) in LOS as a function of the signal-to-noise ratio (SNR) for different coding rates.

FIG. 11 (top) shows the BER results for the downlink, i.e., from the wearable master to the wearable node, and the performance of an uncoded transmission scheme is compared to four coded transmission schemes with coding rates in {8/9, 4/5, 2/3, 1/2}. The information rate for the five transmission schemes ranges from 2.76 kbit/s for the uncoded transmissions to 2.45 kbit/s for coding rate 8/9, 2.20 kbit/s for coding rate 4/5, 1.84 kbit/s for coding rate 2/4, and 1.38 kbit/s for coding rate 1/2. FIG. 11 (bottom) shows the same comparison for the uplink, i.e., from the wearable node to the wearable master. The SNR is calculated at the receiver as the ratio between the received average signal power and the average noise power measured after amplification and high-pass filtering. The measured SNR is varied by reducing the signal power driving the transmitter speaker. In the downlink, this is done by reducing the volume of the smartphone speaker, while in the uplink, the signal full-scale is reduced at the input of the amplifier. The maximum power is selected such that the transmitted sound results are inaudible to people in proximity of the transmitter.

From FIG. 11, it can be observed that, as expected, the BER is a decreasing function of the SNR, and that the FEC scheme mitigates the channel distortion by recovering part of the channel errors. At 5 dB SNR the BER is too high for the FEC to have an impact on the communication performance. Over 5 dB SNR, higher coding rate transmissions have clearly better mitigation performances, thus lower BER.

By measuring the power at the output of the wearable node amplifier, it can be shown how the prototypes achieve 2.76 kbit/s on an uncoded uplink transmission, with a $10^{-5}$ BER, using a transmission power of 20 mW, i.e., 13 dB SNR at the receiver. The transmission power can be lowered by compensating with lower FEC coding rate, thus reducing the information rate. For example, in the current implementation, for a transmission power of 10 mW, i.e., 7 dB SNR, the prototypes achieve 1.38 kbit/s with a $10^{-5}$ BER using a coding rate of 1/2.

By using for the first time a GMSK scheme for the near-ultrasonic frequency range, the prototypes achieve relatively a high-data rate, and ensure virtually inaudible click-free transmission because of the GMSK phase-continuity as discussed in Section 2.1.1.

BER Performance in nLOS.

Figure 12:
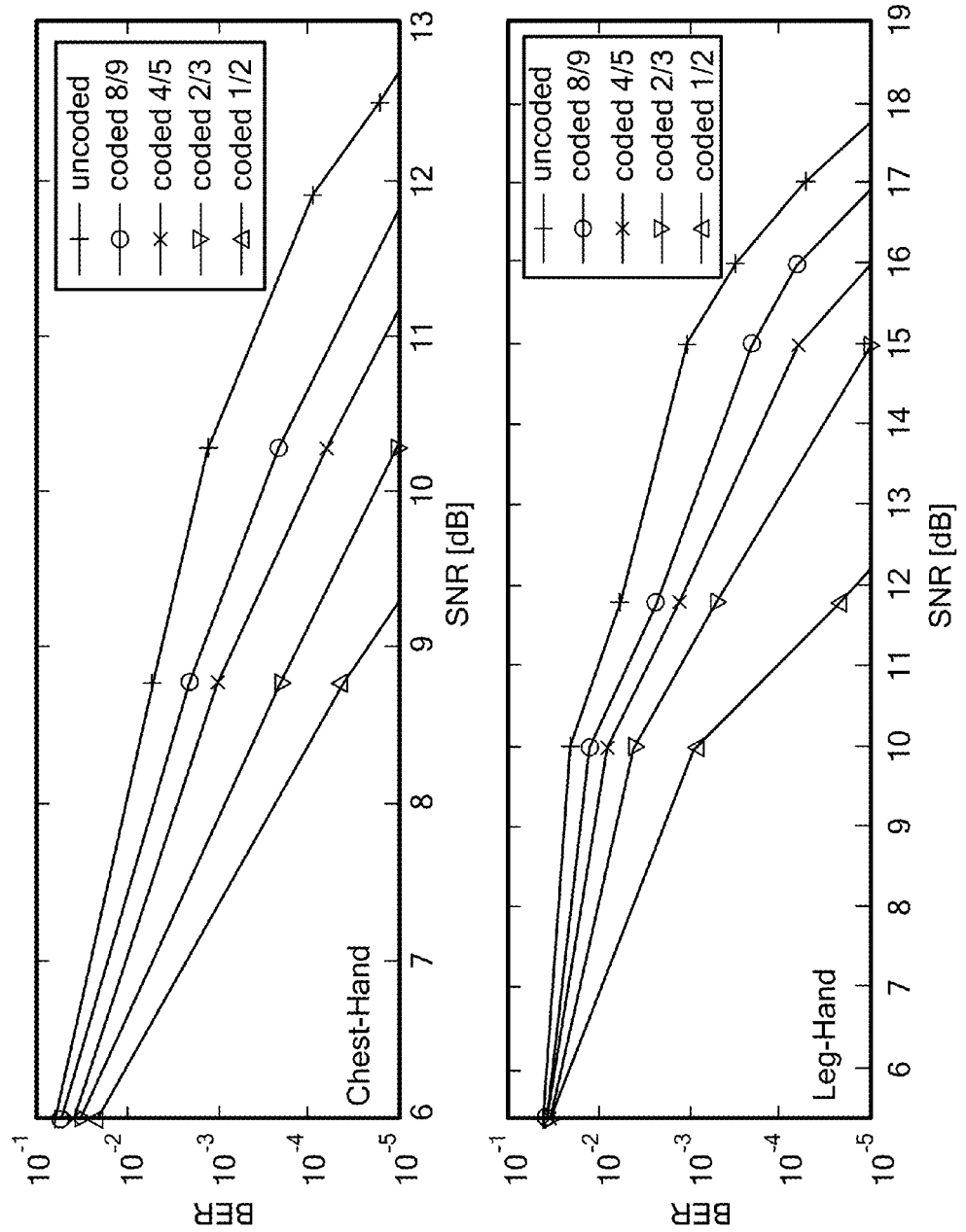
FIG. 12 is a graph of BER of the chest-hand (top) and of the leg-hand uplinks as a function of the SNR for different coding rates.

FIG. 12 shows the BER performance of uplink transmissions in nLOS scenario chest-hand setup (top) and leg-hand setup (bottom). It can be observed that, while the curves follow the same pattern as in the LOS scenario, the corresponding BER levels are higher because of the worse channel conditions. The BER in the chest-hand scenario is slightly higher than the LOS one, i.e., about 1 dB more of SNR is required for the same BER. Differently, in the leg-hand scenario an increase of 4 dB SNR is needed to achieve the same BER performance of the LOS scenario. In the chest-hand uplink, the prototypes achieve 2.76 kbit/s with a $10^{-5}$ BER using a transmission power of 45 mW, i.e., about 13 dB SNR at the receiver, while the same BER is obtained with 45 mW transmission power, i.e., approximately 9 dB SNR at the receiver, halving the data rate through FEC coding. In the leg-hand uplink, $10^{-5}$ BER is obtained with a transmission power of 250 mW, i.e., about 18 dB SNR at the receiver, for uncoded transmission at 2.76 kbit/s, and 130 mW of transmission power, i.e., approximately 12 dB SNR at the receiver, for coded transmission at 1.78 kbit/s.

These results show how multipath effect and higher attenuation caused by the user's clothing require higher power transmission as compared to the LOS scenario. Even though ultrasonic signals are further attenuated by solid materials, they can still be used to communicate over short distances through clothing. In general, the transmission power can be reduced by using speakers and microphones with wider flat bandwidth or custom-made optimized ultrasonic transducers. In fact, a significant portion of the transmission power is lost during the electro-acoustic conversion in the COTS speaker and microphone used in the prototypes, which are not designed to operate efficiently at near-ultrasonic frequencies.

4.2 MAC Layer Performance

The performance of the MAC layer protocols implemented on the prototypes, i.e., polling and ALOHA, was evaluated in terms of data delivery delay, and packet drop rate as a function of the number of nodes in the net-work.

Experiment Setup.

A M/S configuration was set up where devices lay in nLOS on a 2-dimensional surface, and each wearable node was positioned 40 cm apart from the wearable master. The experiment collected data at the wearable master from up to four wearable nodes using polling or ALHOA MAC protocols. Six different parameters were considered than can be fetched, and these were distributed among four wearable nodes, i.e., numbers of footsteps and the number of sleep hours in Node 1, heart rate and the diastolic/systolic blood pressure in Node 2, breath rate/respiratory minute volume in Node 3, and glucose level in the blood in Node 4. Each packet contained 10 bytes of information, i.e., before FEC coding.

Adaptive Polling.

Figure 13:
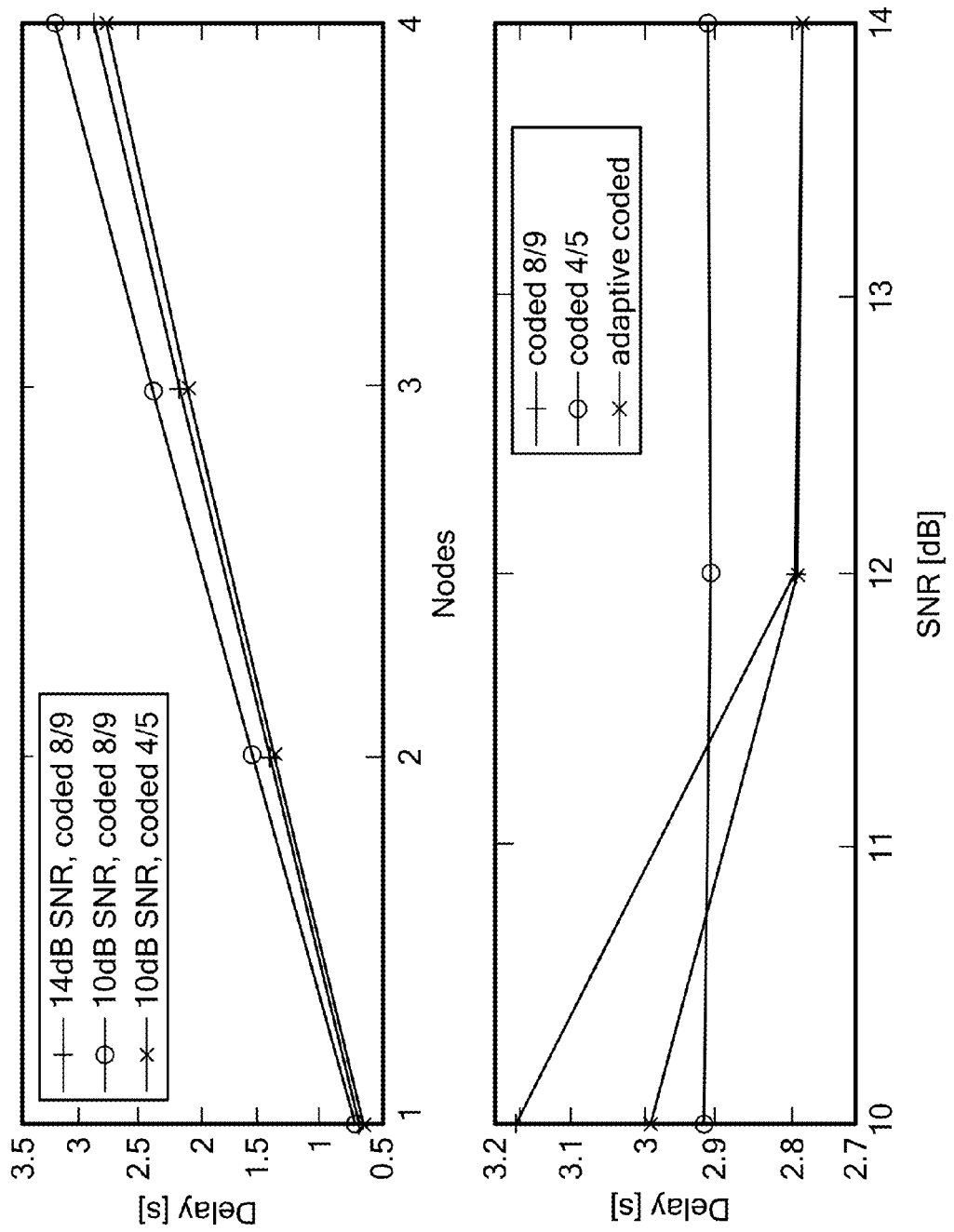
FIG. 13 is a graph of polling data delivery delay as a function of number of nodes for different level of SNR and coding rates (top), and as a function of the SNR for non-adaptive and adaptive scenarios.

Using polling protocol, the wearable master fetched data from one node a time, and wearable nodes were addressed through physical addresses, e.g., node ID. The PHY layer adaptation allowed reactively adapting the FEC coding rate based on the packet drop rate experienced at the wearable master to minimize the number of consecutive retransmissions. Specifically, every time the wearable master retransmitted a fetching packet a lower coding rate was used in {8/9, 4/5, 2/3, 1/2}. The maximum number of retransmissions for each fetch command was fixed to four. The protocol was evaluated in terms of data delivery delay, which was defined as the time between the instant when the first fetching packet is transmitted by the wearable master and the instant when the last data packet is correctly received at the wearable master. FIG. 13 (top) shows the polling data delivery delay as a function of the number of nodes in the network for two levels of SNR measured at the wearable master, i.e., 10 dB and 14 dB, and two coding rates, i.e., 8/9 and 4/5. As expected, since each node in average was granted the same time to transmit, it can be observed that the delivery delay increased linearly with the number of nodes in the network. Moreover, since retransmissions were only caused by the channel conditions, i.e., there were no collisions among different users, the delivery delay decreased by increasing the SNR or the coding rate. FIG. 13 (bottom) shows the delivery delay as a function of the SNR for two fixed coding rates, i.e., 8/9 and 4/5, and for the adaptive scenario. It can be observed that at lower SNR, a coding rate of 8/9 gave delivery delays higher than coding rate 4/5 because of the frequent retransmissions due to higher BER at the PHY layer. On the contrary, for higher SNR, a coding rate of 4/5 introduced more overhead than needed, giving higher delivery delays than a coding rate of 8/9. As expected, the adaptive scenario resulted in delivery delays in between the two fixed coding rate scenarios.

ALOHA.

Figure 14:
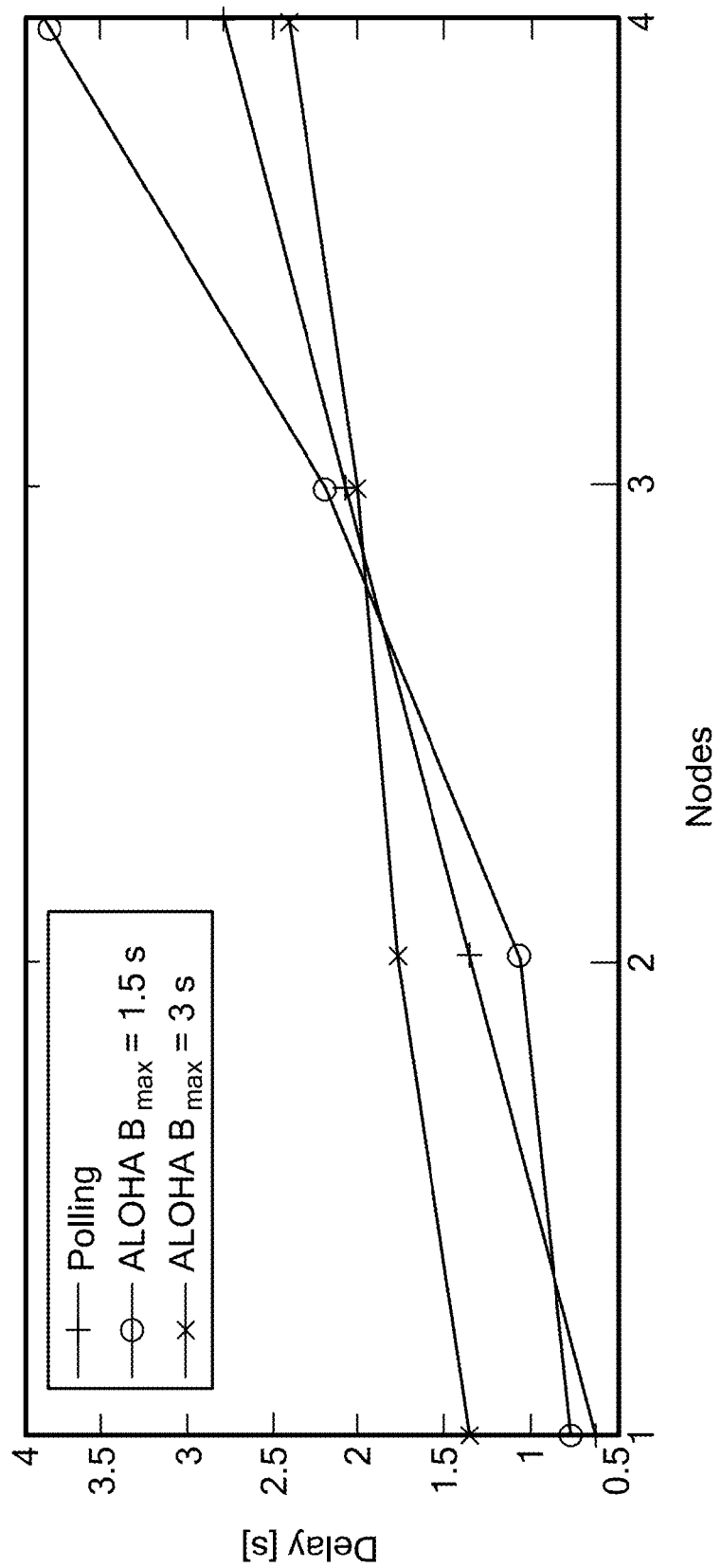
FIG. 14 is a graph of ALOHA data delivery delay as a function of number of nodes for different $B_{max}$, compared to polling.

With ALOHA, the content-centric addressing scheme discussed in Section 3.1.2 was used. Hence, the wearable master broadcast a request message to fetch data from multiple wearable nodes. The wearable nodes transmitted the requested data, if available, by accessing the channel randomly. Finally, the backoff time between transmissions was selected from 0 to a maximum backoff $B_{max}$, and was varied during the experiments, while fixing the SNR to 14 dB and FEC coding rate to 8/9. FIG. 14 shows the data delivery delay as a function of the number of nodes in the network for two different values of $B_{max}$, i.e., 1.5 s and 3 s. The results were compared with the data delivery delay experienced by the polling protocol for 14 dB SNR and 8/9 coding rate. When the number of nodes in the network was lower than three, it can be observed that $B_{max}=1.5$ s gave a lower delay than $B_{max}=3$ s. Here, a higher $B_{max}$ increased the probability of selecting a higher backoff time, leading to channel underutilization. On the other hand, for a number of nodes equal to three or higher, $B_{max}=1.5$ s gave a high probability of collisions, thus a higher delay due to retransmissions.

4.3 Data Processing Performance

To test the effectiveness of the application layer reconfiguration functionalities, the data processing accuracy was evaluated in terms of displacement between the obtained outputs, i.e., what the application reads on a given sensor trace, and the expected ones, i.e., what the application should read on that given sensor trace. Three applications were considered, two running on ECG-equipped sensor nodes, i.e., heart rate monitor, ECG RR interval monitor, and one running on accelerometer-equipped sensor nodes, i.e., footstep counter.

ECG Processing.

To show a fair comparison, the application layer data processing was fed with reference raw sensor data that were externally recorded and then loaded in the wearable node memory. For the ECG-based applications, traces from the MIT-BIH Normal Sinus Rhythm Database were used, which collects ECG recording from patients that were found to have no significant arrhythmias. The MIT-BIH database also specifies heart rate and RR interval of the traces that can be used as a reference. The traces were sampled at 128 Hz. Ten one-minute long traces from the MIT-BIH database were extracted and loaded on the wearable node. Table 1 shows the heart rate estimation of the wearable node using the R method, second column, and RR method, third column, discussed in Section 3.1.2. These were compared with the heart rate reference provided by the MIT-BIH database, fourth column. The first column shows the database trace ID. It can be observed that both R method and RR method give a good estimate of the reference heart rate, offering an average accuracy of 96.1% and 98.7%, respectively.

Table 2 shows the RR interval mean $\mu$ and standard deviation $\sigma$ estimated by the wearable node, second and fourth columns, and compares these with the RR interval reference statistics provided by the MIT-BIH database, third and fifth columns. It can be observed that the wearable node accurately estimates the RR interval mean, i.e., around 99.6% of accuracy. For the standard deviation a, a lower accuracy, i.e., 83.6%, was obtained for two reasons, (i) the relatively low sampling rate gave a sensibility of 8 ms, which can affect the measurement of small quantities such as the standard deviation, and (ii) failures in the peak finding algorithm also affected the measurement. A higher sampling rate and outlier detection techniques can be used to enhance the standard deviation measurement.

TABLE 1

Results for heart-rate (HR) with R and RR method.

| Trace | 6 s R [bpm] | 6 s RR [bpm] | Ref HR [bpm] |
|---|---|---|---|
| 16265 | 100 | 97 | 96 |
| 16272 | 60 | 62 | 62 |
| 16273 | 100 | 97 | 95 |
| 16420 | 90 | 94 | 95 |
| 16483 | 100 | 97 | 97 |
| 16539 | 80 | 80 | 79 |
| 16773 | 70 | 74 | 75 |
| 16786 | 70 | 72 | 71 |
| 16795 | 70 | 67 | 65 |
| 17052 | 70 | 68 | 69 |

TABLE 2

Results for RR interval mean and std. deviation $\sigma$.

| Trace | [s] | $\sigma$ [s] | Ref. [s] | Ref. $\sigma$ [s] |
|---|---|---|---|---|
| 16265 | 0.62 | 0.62 | 0.016 | 0.019 |
| 16272 | 0.96 | 0.96 | 0.109 | 0.115 |
| 16273 | 0.64 | 0.64 | 0.023 | 0.049 |
| 16420 | 0.63 | 0.63 | 0.015 | 0.018 |
| 16483 | 0.62 | 0.62 | 0.015 | 0.012 |
| 16539 | 0.74 | 0.75 | 0.062 | 0.054 |
| 16773 | 0.79 | 0.79 | 0.056 | 0.058 |
| 16786 | 0.85 | 0.84 | 0.046 | 0.036 |
| 16795 | 0.91 | 0.92 | 0.070 | 0.069 |
| 17052 | 0.85 | 0.85 | 0.047 | 0.047 |

Accelerometer Processing.

Ten 3-dimensional accelerometer traces were recorded with a sample rate of 60 Hz using Sensor Log, an iOS app that allows reading sensor data from the device, and exporting them in character-separated values (CSV) format. Sensor Log also provides information about the number of footsteps counted by the iOS device. This was used as a reference to evaluate the accuracy of the footstep counter application in the wearable node. Table 3 shows the footstep count estimated by the wearable node, second column, and compares this with the footstep estimate of the iOS device, third column, and real footstep number counted by the user while performing the steps, fourth column. The first column shows the trace name, which lists 3 walking traces, 3 running traces and 3 stair climbing traces, i.e., downward, upwards and down/upwards. It can be observed that, in average, the wearable node counted footsteps with the same accuracy of the iOS device, i.e., approximately 94% with respect to the number of steps counted by the user.

TABLE 3

Evaluation results for footstep counter.

| Trace | Node | iOS | Real |
|---|---|---|---|
| walk 0 | 44 | 49 | 46 |
| walk 1 | 39 | 39 | 40 |
| walk 2 | 48 | 48 | 50 |
| walk 3 | 38 | 39 | 40 |
| run 0 | 32 | 33 | 34 |
| run 1 | 37 | 42 | 40 |
| run 2 | 32 | 33 | 32 |
| climb up | 19 | 19 | 18 |
| climb down | 17 | 18 | 18 |
| climb do up | 34 | 34 | 39 |

The sensor and/or actuating unit 80 can employ a variety of sensors to sense biological parameters or actuators to actuate biological or medical procedures.

In some embodiments, a sensor can comprise a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, or a sensor for pH, ionic strength or osmolality.

In some embodiments, the sensor for one or more biomolecules can comprise a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

Is some embodiments, the actuator can comprise a drug pump, a heart stimulator, a heart pacemaker, a bone growth stimulator, a deep brain stimulator, a neurostimulator, or a neuromuscular electrical stimulator.

The system and method described herein can be used with humans and non-human animals and can be used in medical and veterinary fields.

The processing unit and communication unit described herein can be part of a computer system that executes programming for controlling the system for transmitting data ultrasonically among wearable devices as described herein. The computing system can be implemented as or can include a computing device that includes a combination of hardware, software, and firmware that allows the computing device to run an applications layer, including the application layer described above, or otherwise perform various processing tasks. Computing devices can include without limitation personal computers, work stations, servers, laptop computers, tablet computers, mobile devices, hand-held devices, wireless devices, smartphones, wearable devices, smart watches, smart clothing, embedded devices, microprocessor-based devices, microcontroller-based devices, programmable consumer electronics, mini-computers, main frame computers, and the like.

The computing device can include a basic input/output system (BIOS) and an operating system as software to manage hardware components, coordinate the interface between hardware and software, and manage basic operations such as start up. The computing device can include one or more processors and memory that cooperate with the operating system to provide basic functionality for the computing device. The operating system provides support functionality for the applications layer and other processing tasks. The computing device can include a system bus or other bus (such as memory bus, local bus, peripheral bus, and the like) for providing communication between the various hardware, software, and firmware components and with any external devices. Any other type of architecture or infrastructure that allows the components to communicate and interact with each other can be used.

Processing tasks can be carried out by one or more processors. Various types of processing technology can be used, including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, drivers, objects, components, data structures, and the like that perform particular tasks or operate on data.

The computing device includes memory or storage, which can be accessed by the system bus or in any other manner. Memory can store control logic, instructions, and/or data. Memory can include transitory memory, such as cache memory, random access memory (RAM), static random access memory (SRAM), main memory, dynamic random access memory (DRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), memory chips, and memristor memory cells. Non-transitory memory can be provided on an external storage device. A computer-readable medium can include any physical medium that is capable of encoding instructions and/or storing data that can be subsequently used by a processor to implement embodiments of the method and system described herein. Any other type of tangible, non-transitory storage that can provide instructions and/or data to a processor can be used in these embodiments.

The computing device can include one or more input/output interfaces for connecting input and output devices to various other components of the computing device. Input and output devices can include, without limitation, keyboards, mice, joysticks, microphones, displays, touchscreens, monitors, scanners, speakers, and printers. Interfaces can include universal serial bus (USB) ports, serial ports, parallel ports, game ports, and the like. Other hardware components and devices can interface with the computing device. As used herein, the term "transceiver" can include one or more devices that both transmit and receive signals, whether sharing common circuitry, housing, or a circuit board, or whether distributed over separated circuitry, housings, or circuit boards, and can include a transmitter-receiver.

The computing device can access a network over a network connection that provides the computing device with telecommunications capabilities. Network connection enables the computing device to communicate and interact with any combination of remote devices, remote networks, and remote entities via a communications link. The communications link can be any type of communication link, including without limitation a wired or wireless link. For example, the network connection can allow the computing device to communicate with remote devices over a network, which can be a wired and/or a wireless network, and which can include any combination of intranet, local area networks (LANs), enterprise-wide networks, medium area networks, wide area networks (WANs), the Internet, cellular networks, and the like. Control logic and/or data can be transmitted to and from the computing device via the network connection.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A system for transmitting data ultrasonically among wearable devices comprising:
a network comprising a plurality of nodes, at least a portion of the nodes wearable by a user, each of the wearable nodes including a wearable sensor or a wearable actuator; and a first node of the plurality of nodes comprising:
a communication unit comprising an ultrasonic transceiver to transmit and receive in-air ultrasonic signals;
a processing unit in communication with the communication unit to receive signals from and transmit signals to the communication unit, the processing unit including one or more processors and memory; and
a protocol stack disposed within the processing unit, the protocol stack comprising a plurality of layers through which a data packet is transmitted to enable ultrasonic communication among the plurality of nodes, wherein the protocol stack includes a physical layer, a data link layer, a network layer, and an application layer.

2. The system of claim 1, wherein at least one of the nodes of the plurality of nodes is implantable within a body.

3. The system of claim 1, wherein the processing unit is operative at the application layer of the protocol stack to reconfigure parameters at a physical layer of the protocol stack.

4. The system of claim 1, wherein the processing unit is operative at the application layer of the protocol stack to execute an application.

5. The system of claim 1, wherein the processing unit is operative at the application layer to specify an input comprising data generated at a sensor associated with a wearable node or an output comprising a measured parameter for storage in the memory or transmission to another node.

6. The system of claim 1, wherein the ultrasonic transceiver comprises an air-coupled ultrasonic transducer, a micromachined piezoelectric, or an electrostatic transducer.

7. The system of claim 1, wherein the processing unit is operative at the application layer to carry out one or more data processing operations.

8. The system of claim 7, wherein each data processing operation is identified with a key, and a concatenation of keys forms an application.

9. The system of claim 7, wherein the data processing operations are defined by one or more primitive blocks at a physical layer of the protocol stack, the primitive blocks comprising one or more of a filter, a data operation block, and a detector; and
wherein:
the filter is operative to filter raw data to remove one or more of offset, drift of a sensor, or a noise component from an external source; or
the data operation block is operative to perform one or more signal processing operations on data received from a sensor, wherein the signal processing operations include an arithmetic operation, a correlation operation, a convolution operation, a counting operation, or a Fourier transform operation; or
the detector is operative to measure a desired parameter in a processed signal, wherein the desired parameter includes one or more of a peak, a pattern, or a time interval.

10. The system of claim 9, wherein the processing unit is operative at the application layer to arrange a plurality of the primitive blocks in a user-selected order.

11. The system of claim 1, wherein the first node comprises a wearable node.

12. The system of claim 1, wherein:
the wearable sensor comprises a sensor operative to sense a biological parameter, wherein the wearable sensor is selected from the group consisting of a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality; or the wearable actuator is selected from the group consisting of a drug pump, a heart stimulator, a heart pacemaker, a bone growth stimulator, a deep brain stimulator, a neurostimulator, and a neuromuscular electrical stimulator.

13. The system of claim 1, wherein the plurality of nodes are connected in one or both of a peer-to-peer configuration and a master-slave configuration, wherein the first node comprises a master node in the master-slave configuration, wherein the master node is disposed on an external computing device, wherein the external computing device comprises a smart phone, a tablet, a laptop, a smart watch, smart glasses, or smart clothing.

14. The system of claim 1, wherein the processing unit is operative at the application layer to fetch data from an external source or from another node in the network, and to push data or an actuating command to another node in the network.

15. The system of claim 1, wherein the processing unit is operative at the application layer to provide a graphical user interface to display a selection of applications or functionalities within the protocol stack.

16. The system of claim 1, wherein the processing unit is operative at a physical layer of the protocol stack to provide forward error correction.

17. The system of claim 1, wherein the processing unit is operative at a physical layer of the protocol stack to provide a zero-forcing equalizer comprising a finite-impulse-response filter that for each input symbol, forces to zero any intersymbol interference components introduced by adjacent symbols.

18. The system of claim 1, wherein the processing unit is operative at a physical layer of the protocol stack to calculate filter taps numerically beginning from an estimate of a channel impulse response.

19. The system of claim 1, wherein the processing unit is operative at a physical layer of the protocol stack to provide a pseudo noise sequence or a chirp signal as a preamble of the data packet.

20. The system of claim 1, wherein the processing unit is operative at a physical layer of the protocol stack to correlate a received signal with a known preamble sequence to obtain an estimate of a time-domain channel impulse response.

21. The system of claim 1, wherein the processing unit is operative at a physical layer of the protocol stack to provide narrow band Gaussian minimum shift keying (GMSK) modulation or demodulation or to provide wideband orthogonal frequency division multiplexing for modulation or demodulation.

22. The system of claim 1, wherein the processing unit is operative at upper layers of the protocol stack to modify one or more parameters at a physical layer of the protocol stack, the parameters comprising a modulation rate, a signal bandwidth, and forward error correction coding rate.

23. The system of claim 1, wherein the processing unit is operative at a data link layer of the protocol stack to coordinate access to communication links among the nodes.

24. The system of claim 1, wherein the processing unit is operative at a network layer of the protocol stack to provide content centric addressing, comprising providing a content object at one of the nodes with an identification by which the content object can be accessed by others of the nodes, or to provide header information for transmission to a device on another network.

25. A method for transmitting data ultrasonically among wearable devices comprising:
providing a node comprising:
a communication unit comprising an ultrasonic transceiver to transmit and receive in-air ultrasonic signals, and
a processing unit in communication with the communication unit, comprising one or more processors and memory, and a protocol stack comprising a plurality of layers through which a data packet is transmitted to enable ultrasonic communication among the plurality of nodes;
coding or decoding a data packet by transmission through the layers of the protocol stack within the processing unit, wherein the protocol stack includes a physical layer, a data link layer, a network layer, and an application layer; and
transmitting an ultrasonic signal to or receiving an ultrasonic signal from another node.

* * * * *